(12) United States Patent
Ghandi et al.

(10) Patent No.: US 9,982,073 B2
(45) Date of Patent: May 29, 2018

(54) HOMOPOLYMERS OF TERPENOID ALCOHOLS AND THEIR USES

(71) Applicants: Khashayar Ghandi, Sackville (CA); Zahid Shabbir Mahimwalla, Sackville (CA); Jodi Rose Gallinger, Sackville (CA); Garrett Muir, Halifax (CA)

(72) Inventors: Khashayar Ghandi, Sackville (CA); Zahid Shabbir Mahimwalla, Sackville (CA); Jodi Rose Gallinger, Sackville (CA); Garrett Muir, Halifax (CA)

(73) Assignee: Khashayar Ghandi, Sackville, New Brunswick (CA)

( * ) Notice: Subject to any disclaimer, the term of this patent is extended or adjusted under 35 U.S.C. 154(b) by 0 days. days.

(21) Appl. No.: 15/082,411

(22) Filed: Mar. 28, 2016

(65) Prior Publication Data

US 2016/0280818 A1   Sep. 29, 2016

Related U.S. Application Data

(60) Provisional application No. 62/139,129, filed on Mar. 27, 2015.

(51) Int. Cl.

| | | |
|---|---|---|
| *C08F 136/14* | (2006.01) | |
| *C08F 110/14* | (2006.01) | |
| *A01N 49/00* | (2006.01) | |
| *A61K 8/81* | (2006.01) | |
| *A61Q 19/00* | (2006.01) | |

(52) U.S. Cl.
CPC ............ *C08F 136/14* (2013.01); *A01N 49/00* (2013.01); *A61K 8/8129* (2013.01); *A61K 8/8194* (2013.01); *A61Q 19/00* (2013.01); *C08F 110/14* (2013.01); *A61K 2800/77* (2013.01); *A61L 2300/404* (2013.01)

(58) Field of Classification Search
CPC .... A01N 49/00; A61K 8/8129; A61K 8/8194; A61K 2800/77; A61Q 19/00; C08F 110/14; C08F 136/14; A61L 2300/404
See application file for complete search history.

(56) References Cited

U.S. PATENT DOCUMENTS

| | | |
|---|---|---|
| 7,776,959 B2 | 8/2010 | Coca et al. |
| 2012/0213727 A1 | 8/2012 | Hazan |
| 2015/0079021 A1 | 3/2015 | Hazan |

FOREIGN PATENT DOCUMENTS

WO    WO 2014201544 A1 * 12/2014 ........... A61L 29/085

OTHER PUBLICATIONS

Jacob, M. V. et al. "Plasma polymerised thin films for flexible electronic applications" Thin Solid Films 546 (2013) 167-170.*
Lee, S. Encyclopedia of Chemical Processing 2006, vol. 4, pp. 1-4.*
Easton, C. D. et al. "RF plasma polymerised thin films from natural resources" International Journal of Modern Physics: Conference Series vol. 32 (2014) pp. 1-10.*

(Continued)

*Primary Examiner* — Medhanit W Bahta
(74) *Attorney, Agent, or Firm* — Bereskin & Parr LLP/S.E.N.C.R.L., s.r.l.; Michael Fenwick

(57) ABSTRACT

The present disclosure relates to the homopolymerization of terpenoids containing an alcohol functional group by free radical polymerization.

15 Claims, 29 Drawing Sheets

(56) References Cited

OTHER PUBLICATIONS

Figure 1:
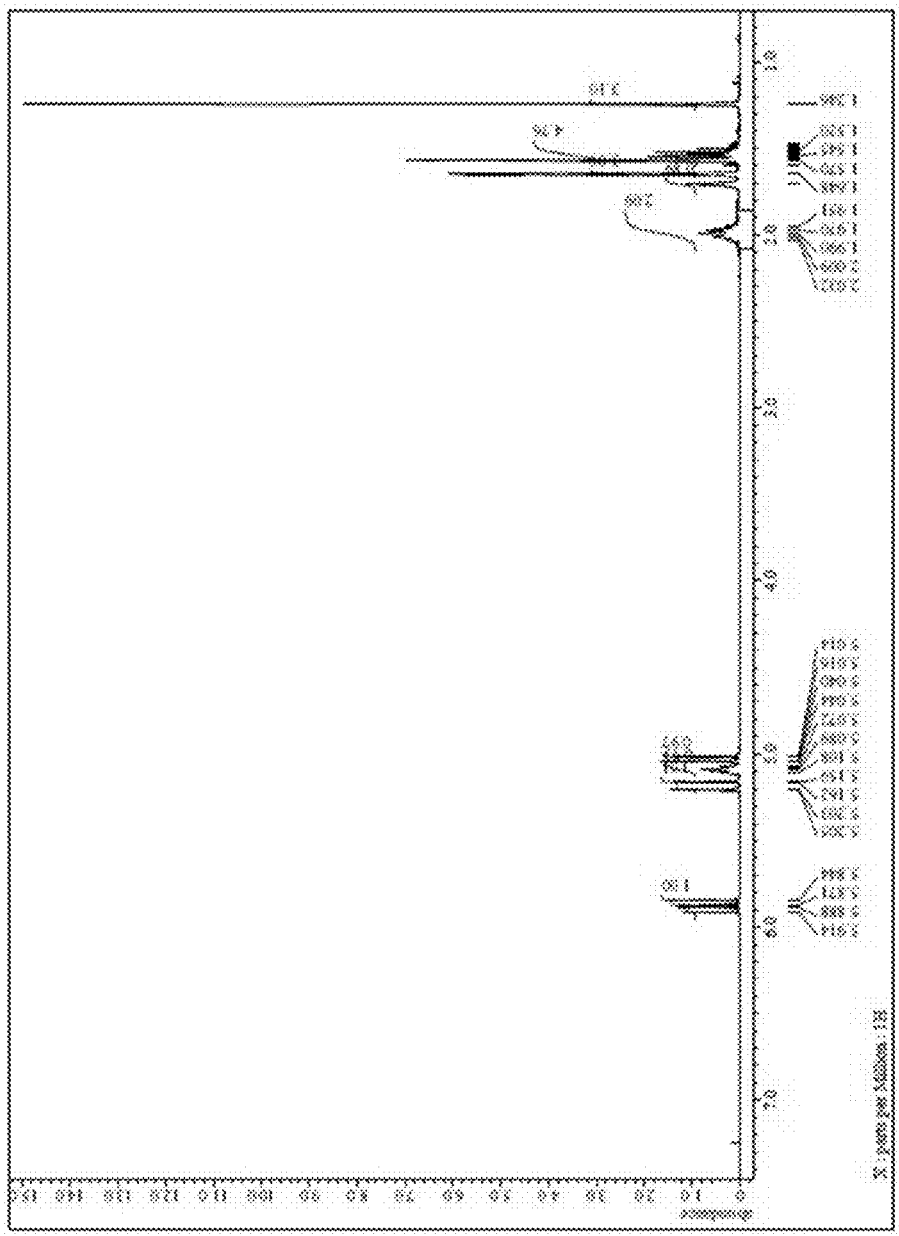

Bazaka, K. et al. "Fabrication and Characterization of RF Plasma Polymerized Thin Films from 3,7-Dimethyl-1,6-octadien-3-ol for Electronic and Biomaterial Applications" Advanced Materials Research Online: Aug. 11, 2010, vols. 123-125, pp. 323-326.*

Dorman, H. J.; Deans, S. G. Antimicrobial Agents from Plants: Antibacterial Activity of Plant Volatile Oils. J. Appl. Microbiol. 2000, 88, 308-316.

Tang, H.; Murphy, C. J.; Zhang, B.; Shen, Y.; Van Kirk, E. a; Murdoch, W. J.; Radosz, M. Curcumin Polymers as Anticancer Conjugates. Biomaterials 2010, 31, 7139-7149.

Taylor, P.; Dorman, H. J. D.; Surai, P.; Deans, S. G. Journal of Essential Oil Research In Vitro Antioxidant Activity of a Number of Plant Essential Oils and Phytoconstituents In Vitro Antioxidant Activity of a Number of Plant Essential Oils and Phytoconstituents. J. Essent. Oil Res. 2000, 12, 241-248.

Wilbon, P. A.; Chu, F.; Tang, C. Progress in Renewable Polymers from Natural. Marcomelecular Rapid Commun. 2013, 34, 8-37.

Blazquez, C.H., Vidyarthi, A.D., Sheehan, T.D. Bennett, M.J. and McGraw, G.T. Agricultural, F.; Stations, E.; Series, J.; Florida, S. Effect of Pinolene ( ,8-Pinene Polymer) on Carbaryl Foliar Residues. J. Agric. Food Chem. 1970, 18, 681-684.

Singh, A.; Dwivedi, M. K; Singh, D. K. Kinetic Study of Copolymerization of Linalool and Methyl Methacrylate Initiated by Selenonium Ylide. Int. J. Chem. Kinet. 2011, 43, 43-52.

Shukla, A.; Srivastava, A. K. Synthesis and Characterization of Functional Copolymer of Linalool and Vinyl Acetate: A Kinetic Study. J. Appl. Polym. Sci. 2004, 92, 1134-1143.

Shukla, A.; Srivastava, A. K. Determination of Reactivity Ratios and Kinetics of Free Radical Copolymerization of Linalool with Styrene. Polym. Adv. Technol. 2004, 15, 445-452.

Shukla, A.; Srivastava, a. K. Kinetics and Mechanism of Copolymerization of Linalool with Acrylonitrile. J. Macromol. Sci. Part A 2003, 40, 61-80.

Shukla, A.; Srivastava, A. K. Free Radical Copolymerization of Acrylamide and Linalool with Functional Group as a Pendant. High Perform. Polym. 2003, 15, 243-257.

Bower, D. I. The Vibrational Spectroscopy of Polymers; Cambridge University Press, 1992; pp. 15-16.

Dohmen, M. P. J.; Pereira, A. M.; Timmer, J. M. K.; Benes, N. E.; Keurentjes, J. T. F. Hydrodynamic Radii of Polyethylene Glycols in Different Solvents Determined from Viscosity Measurements. J. Chem. Eng. Data 2008, 53, 63-65.

Khashayar Ghandi and Zahid Mahimwalla. Plasma Induced Thin Films of Linalool Are Not Polylinaool. MOJ Biol. Med. 1(2), 2017.

Damien Thiry, Stephanos Konstatinidis, Jerome Cornil and Rony Synders. Plasma Diagnostics for the Low-Pressure Plasma Polymerization Process: A Critical Review. Thin Solid Films, 606:19-44, 2016.

* cited by examiner

HOMOPOLYMERS OF TERPENOID ALCOHOLS AND THEIR USES

CROSS-REFERENCE TO OTHER APPLICATIONS

The present application claims the benefit of provisional patent application No. 62/139,129, filed Mar. 27, 2015, the contents of which is herein incorporated by reference.

FIELD

The present disclosure relates to the field of polymerization, mainly the homopolymerization of terpenoids containing an alcohol group via a free radical polymerization mechanism.

INTRODUCTION

In the scientific and patent literature there is a need for new renewable polymers and polymeric materials. Terpenes and terpenoids are a large class of biological compounds with one or more isoprene units that have generated significant interest as monomers for polymerization. Terpenes and terpenoids have many desirable properties including antimicrobial[1], anticancer[2], and antioxidant[3] activity. However, they are often volatile or water insoluble which can make them less useful for some applications.[2] Polymerization of these compounds is one possible route to improving their physical properties while retaining their desirable chemical properties, because larger molecules are less volatile and various functional groups can be incorporated into polymers to alter other physical properties such as solubility. Polymers and co-polymers of terpenes have found numerous uses in coatings (U.S. Pat. No. 7,776,959 B2), therapeutic agents (US20120213727 A1), pharmaceuticals,[2,4] green plastics[5] and pesticides.[6]

The polymerization of these monomers has involved different chemical strategies. As reviewed reviewed by Wilbon et al.[5] Terpenes and terpenoids have been both homo and copolymerized for a variety of applications. However, the polymerization of terpenoids is difficult.

It has been proposed to be impossible to homopolymerize acyclic monoterpenoids via a free radical polymerization mechanism, based on the previous reports in the literature.[7-11]

Accordingly there is a need to develop techniques for homopolymerizing terpenoids, which are chemically different from terpenes due to the inclusion of one or more oxygen containing functional group(s). These materials have been considered extremely difficult to homopolymerize via a free radical mechanism to yield useful functional materials as significant chemical modification of the monomer is usually required prior to polymerization[5].

SUMMARY

The present disclosure relates to the homopolymerization of terpenoids containing at least one alcohol group using free radical polymerization. Terpenoids with alcohol containing groups, in particular acyclic monoterpenoids, have been considered by the scientific literature to be impossible to homopolymerize via free radical chemistry without significant chemical modification of the monomers.

These terpenoids are natural, plant based compounds with numerous uses including therapeutic, antimicrobial, scent, flavor, and insecticidal. However, they are often volatile which can reduce their utility in some applications. Polymerization offers a method to improve their use by reducing volatility and modifying the physical properties of the material to be more desirable from an applications perspective. Polymerization can also potentially enhance the therapeutic, antimicrobial and other desirable properties of these materials. Such polymers would also contain multiple functional groups (polyols etc.) that can then be used as renewable prepolymers for urethane and other chemistry.

In one embodiment of the disclosure, there is included a terpenoid homopolymer having the general representative structure (I) or (II)

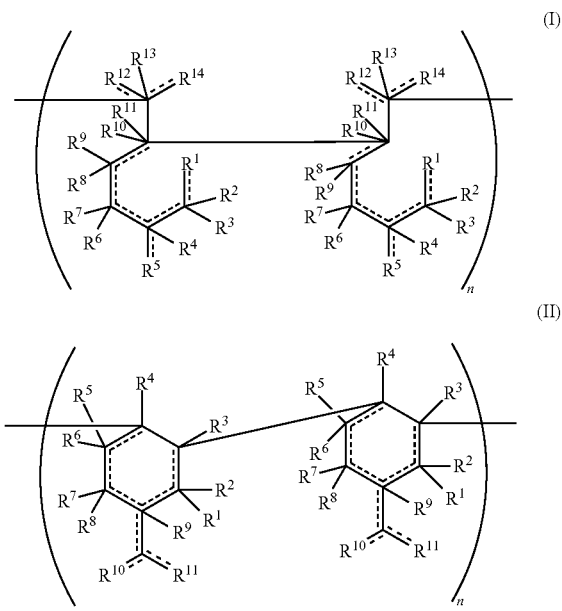

wherein the broken lines represent either a carbon-carbon single or double bond, with at least one carbon double bond being present in the structure, n is an integer between 1 and 10,000;

$R^1$ to $R^{14}$ are independently or simultaneously H, halo, ($C_1$-$C_{24}$)-alkyl, ($C_2$-$C_{24}$)-alkenyl, ($C_2$-$C_{24}$)-alkynyl, ($C_6$-$C_{14}$)-aryl or ($C_5$-$C_{14}$)-heteroaryl, wherein the latter 5 groups are optionally substituted and wherein the optional substituents are chosen from one or more of halogen, —OH, ($C_1$-$C_6$)-alkyl, ($C_1$-$C_6$)-alkoxy, thionyl, nitro, amino (—$NH_2$), ($C_6$-$C_{14}$)-aryl, ($C_5$-$C_{14}$)-heteroaryl, phosphate (—$PO_4$), and phosphoryl (—$PO_3$), wherein at least one of $R^1$-$R^{14}$ contains at least one —OH group;

and wherein $R^1$-$R^{14}$ can also optionally comprise one or more isoprene subunits according to the general structure

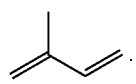

In one embodiment of the disclosure, there is included a terpenoid homopolymer having the general representative structure (I) or (II)

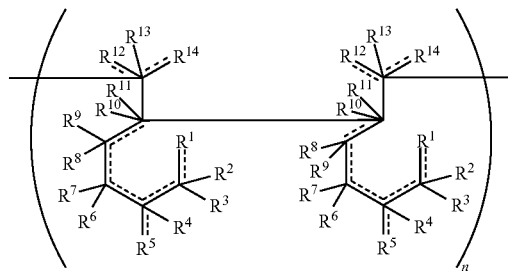

(I)

(II)

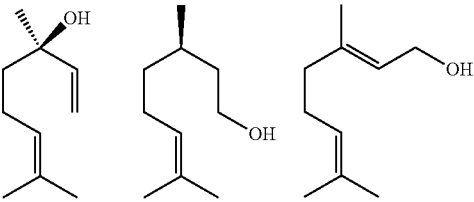

Linalool     Cironello     Geraniol

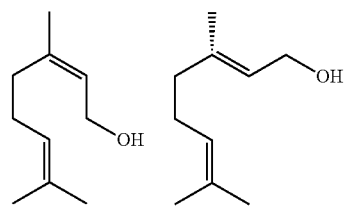

Nerol     Rhodinol

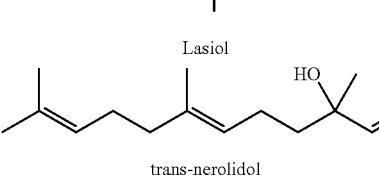

Lasiol

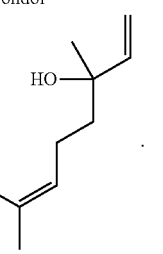

trans-nerolidol cis-nerolidol

In one embodiment, the homopolymer is comprised of covalently joined terpenoid monomers having the general structures

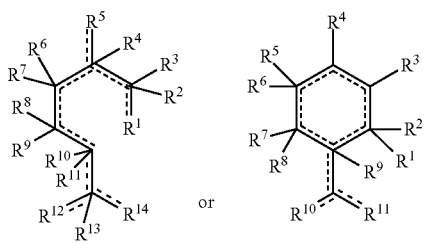

wherein R1-R14 and the dashed lines are as defined above.

In one embodiment, $R^1$ to $R^{14}$ are independently or simultaneously H, halo, $(C_1-C_{10})$-alkyl, $(C_2-C_{10})$-alkenyl, $(C_2-C_{10})$-alkynyl, $(C_6-C_{10})$-aryl or $(C_5-C_{10})$-heteroaryl. In another embodiment, $R^1$ to $R^{14}$ are independently or simultaneously H, halo, $(C_1-C_6)$-alkyl, $(C_2-C_6)$-alkenyl, $(C_2-C_6)$-alkynyl, $(C_6)$-aryl or $(C_5-C_6)$-heteroaryl. In another embodiment, $R^1$ to $R^{14}$ are independently or simultaneously H or $(C_1-C_6)$-alkyl, In one embodiment, the terpenoid monomer is optionally a cyclic terpenoid, a poly-cyclic terpenoid, an acyclic terpenoid, or a terpenoid consisting of between 1 to 8 linked isoprene subunits.

In one embodiment, the terpenoid monomer is an acyclic monoterpenoid.

In one embodiment, the acyclic monoterpenoid monomer is chosen from the group consisting of geraniol, citronellol, linalool, nerol, rhodinol, lasiol, trans and cis nerolidol having the following structures In one embodiment, the cyclic terpenoid is chosen from terpineol and its isomers.

In one embodiment, n is an integer between about 5 and about 1,000.

In one embodiment, n is an integer between about 5 and about 15.

In one embodiment, the terpenoid homopolymer is a functional polyol pre-polymer.

In one embodiment, the terpenoid homopolymer is a functional pre-polymer for urethane chemistry.

In one embodiment, the terpenoid homopolymer has therapeutic, antimicrobial or insecticidal properties.

In one embodiment, the terpenoid homopolymer has preservative properties.

In one embodiment, the terpenoid homopolymer is incorporated as an organoleptic agent in a cosmetic formulation In one embodiment, the terpenoid homopolymer is incorporated into a finished consumer product or packaging materials to impart antimicrobial or organoleptic properties to the material.

In one embodiment, the terpenoid homopolymer forms a liquid antimicrobial coating by non-covalently bonding to the desired surface or substrate.

In one embodiment, the antimicrobial terpenoid homopolymer is incorporated into bandages, shrink coatings, polymeric and other composite materials for medicinal, protective coatings and packaging applications.

In one embodiment, the terpenoid homopolymer is applied as a film or surface coating by chemical functionalization or reactions of the hydroxyl group with the surface.

In one embodiment, the terpenoid homopolymer is a feedstock for renewable plastic materials.

There is also included a method of synthesizing a terpenoid homopolymer as defined in claim 1, comprising homopolymerizing a terpenoid monomer comprising at least one double bond, conjugated double bond or aromatic double bond and at least one hydroxyl functional group by free radical polymerization, the method comprising i. Reacting the monomer with a free radical initiator without deprotonation or without protecting groups;

ii. Optionally deprotonating or protecting the hydroxyl functionality of the monomer prior to polymerization.

In one embodiment, the free radical initiator is selected from hydrogen peroxide, an azo initiator, a halogen initiator, an organic peroxide initiator, an inorganic peroxide initiator, a hydroxyperoxy initiator, a photosensitizer, a photo initiator and a transition metal catalyst capable of generating radicals for polymerization.

In one embodiment, the polymerization is initiated thermally or photoinitiated.

In one embodiment, the reaction is conducted in a solvent.

DRAWINGS

FIG. 1. A $^1$H nuclear magnetic resonance spectrum (NMR) of linalool with $CDCl_3$ as the solvent.

Figure 2:
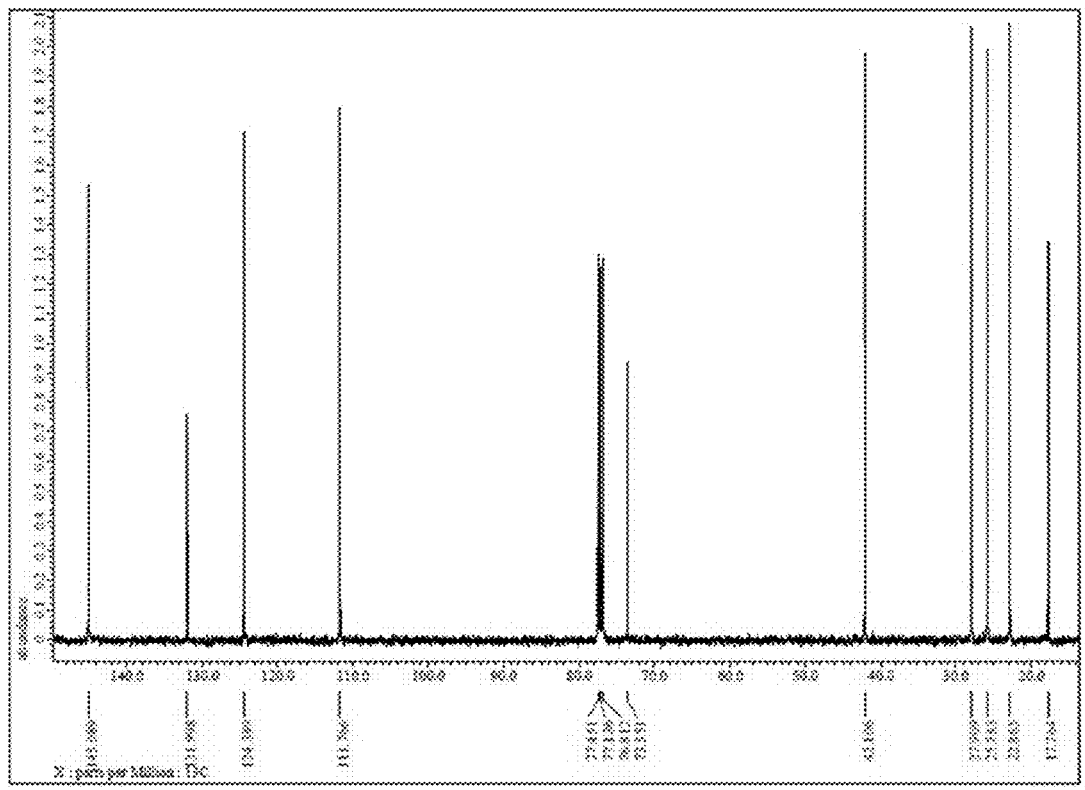

FIG. 2. A $^{13}$C nuclear magnetic resonance spectrum (NMR) of linalool with $CDCl_3$ as the solvent.

Figure 3:
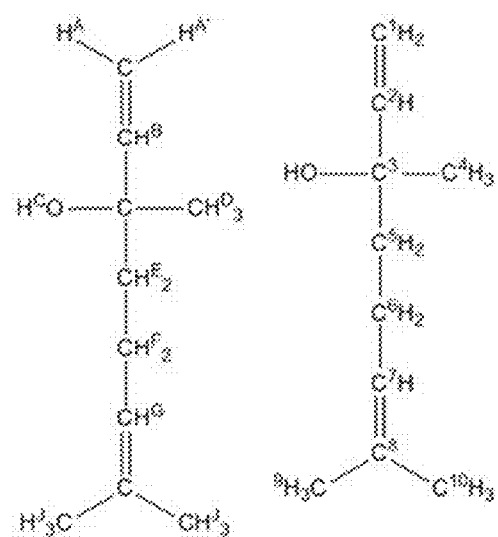

FIG. 3. A chemical structure of linalool with hydrogens labelled a-i and carbon atoms numbered 1-10 to correspond to NMR peaks.

Figure 4:
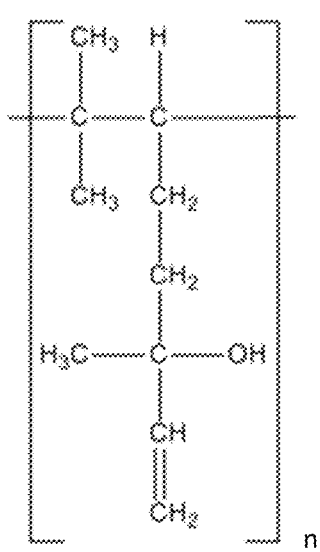

FIG. 4. A chemical structure of a proposed linalool homopolymer.

Figure 5:
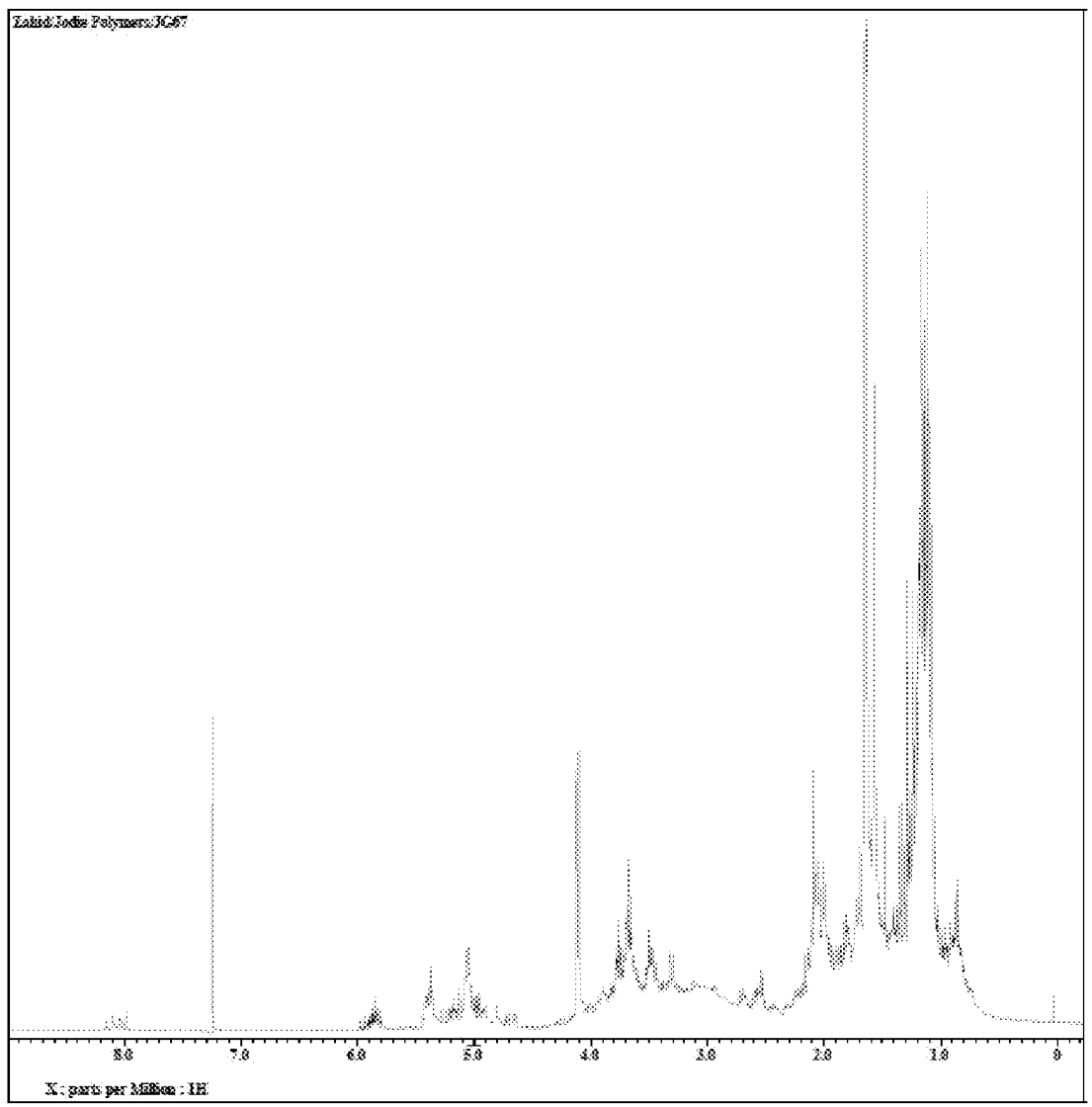

FIG. 5. A $^1$H nuclear magnetic resonance spectrum (NMR) of a linalool homopolymer with $CDCl_3$ as the solvent.

Figure 6:
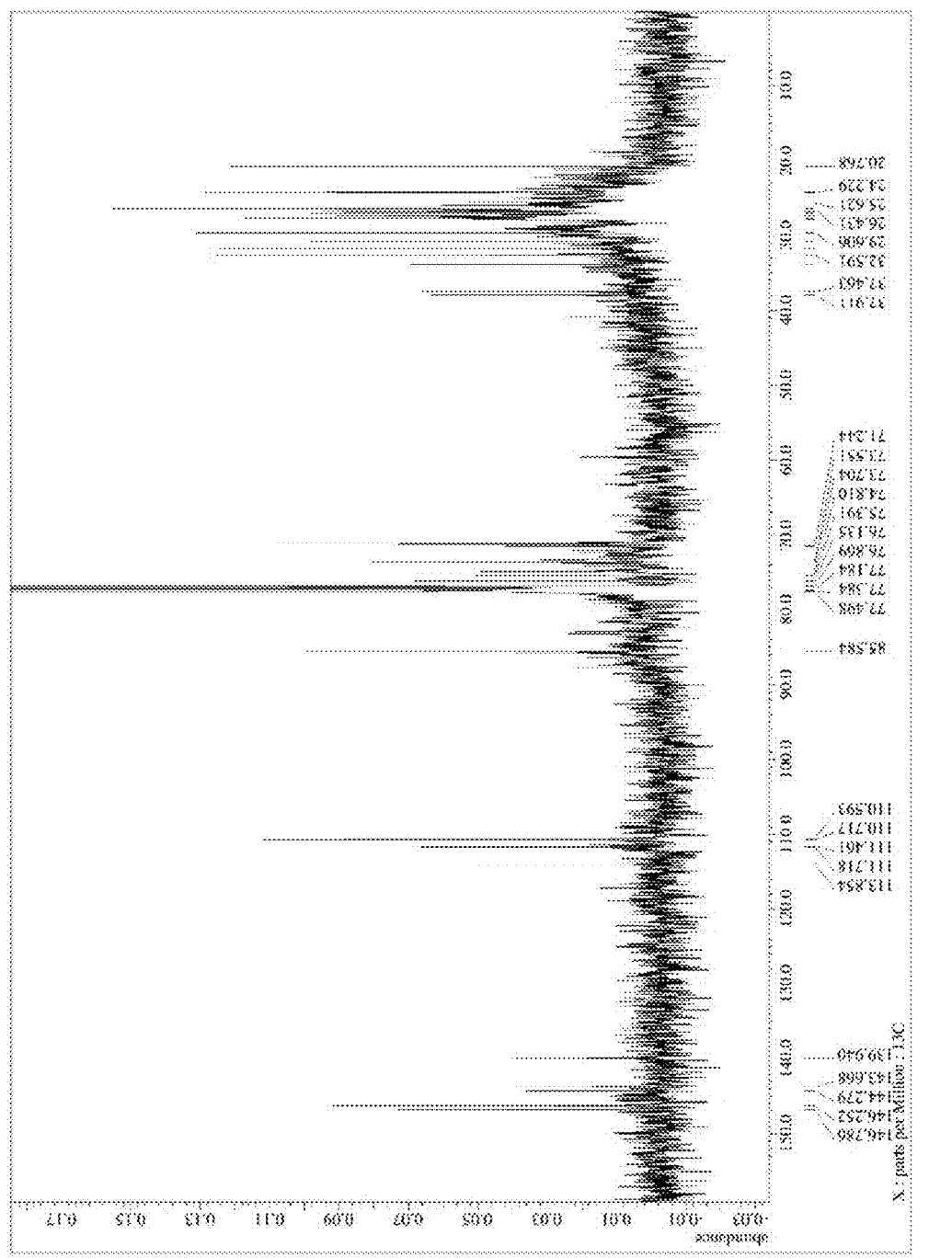

FIG. 6. A $^{13}$C nuclear magnetic resonance spectrum (NMR) of linalool with $CDCl_3$ as the solvent.

Figure 7:
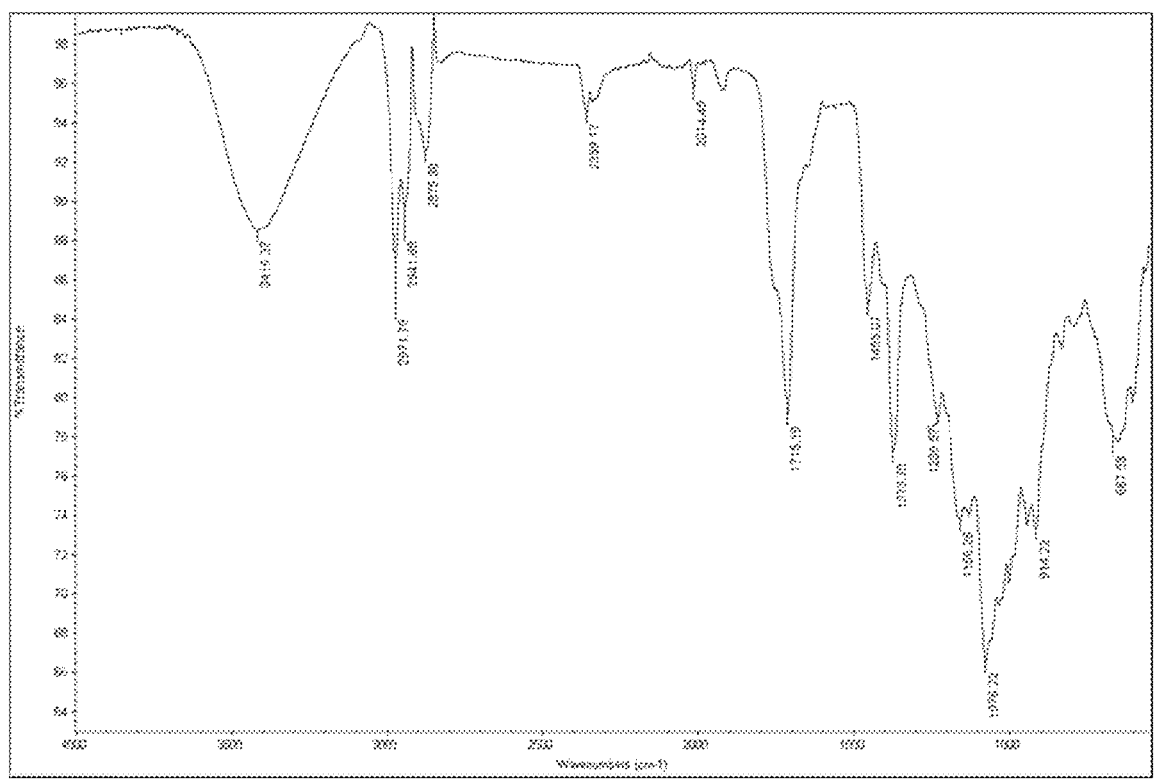

FIG. 7. A fourier transform infra-red spectrum (FTIR) of a linalool homopolymer.

Figure 8:
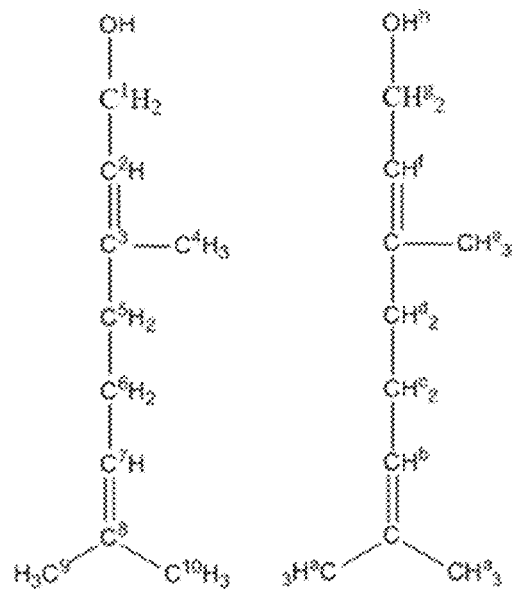

FIG. 8. A chemical structure of geraniol with hydrogens labelled a-h and carbon atoms numbered 1-10 to correspond to NMR peaks.

Figure 9:
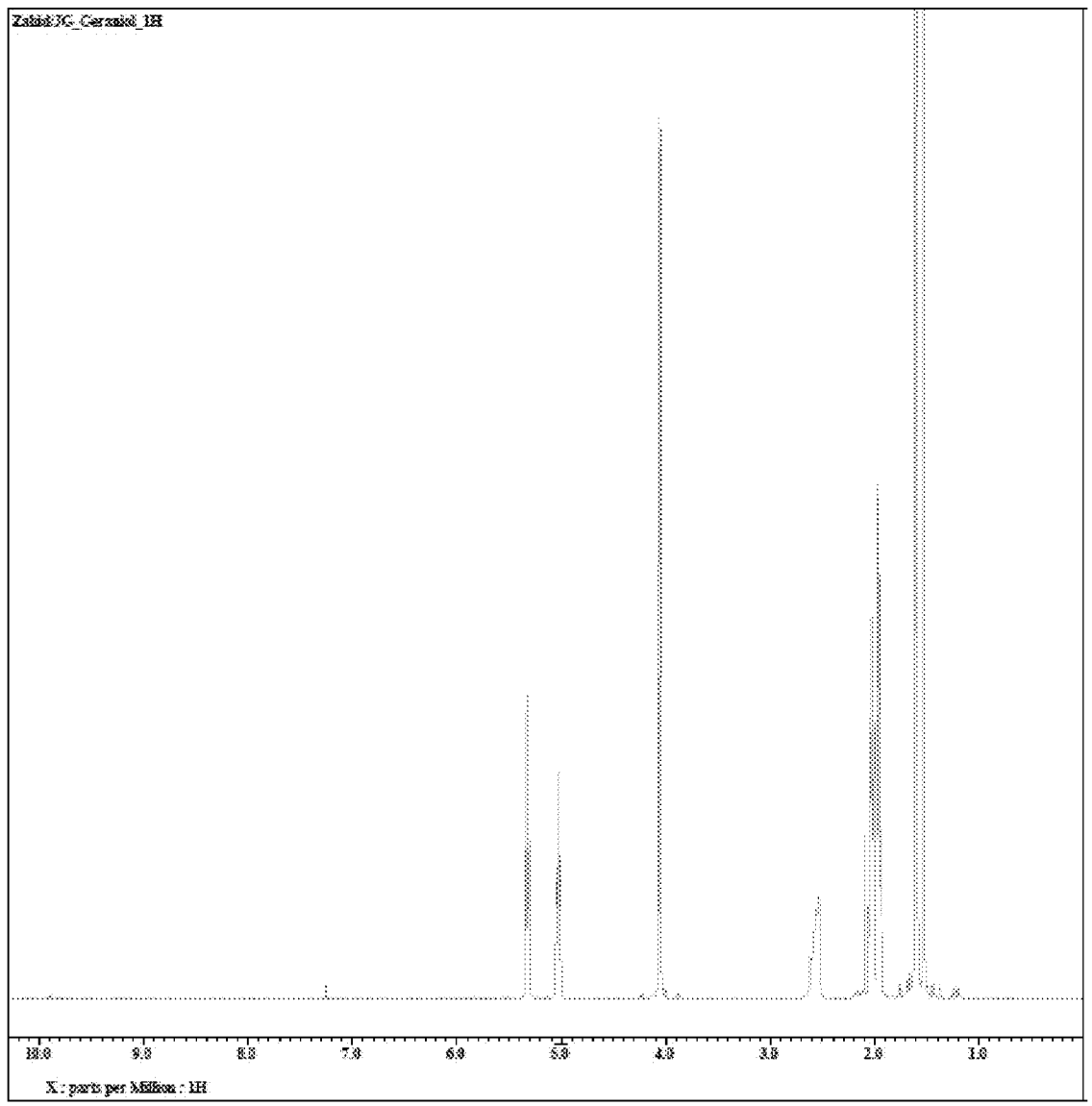

FIG. 9. A $^1$H nuclear magnetic resonance spectrum (NMR) of geraniol with $CDCl_3$ as the solvent.

Figure 10:
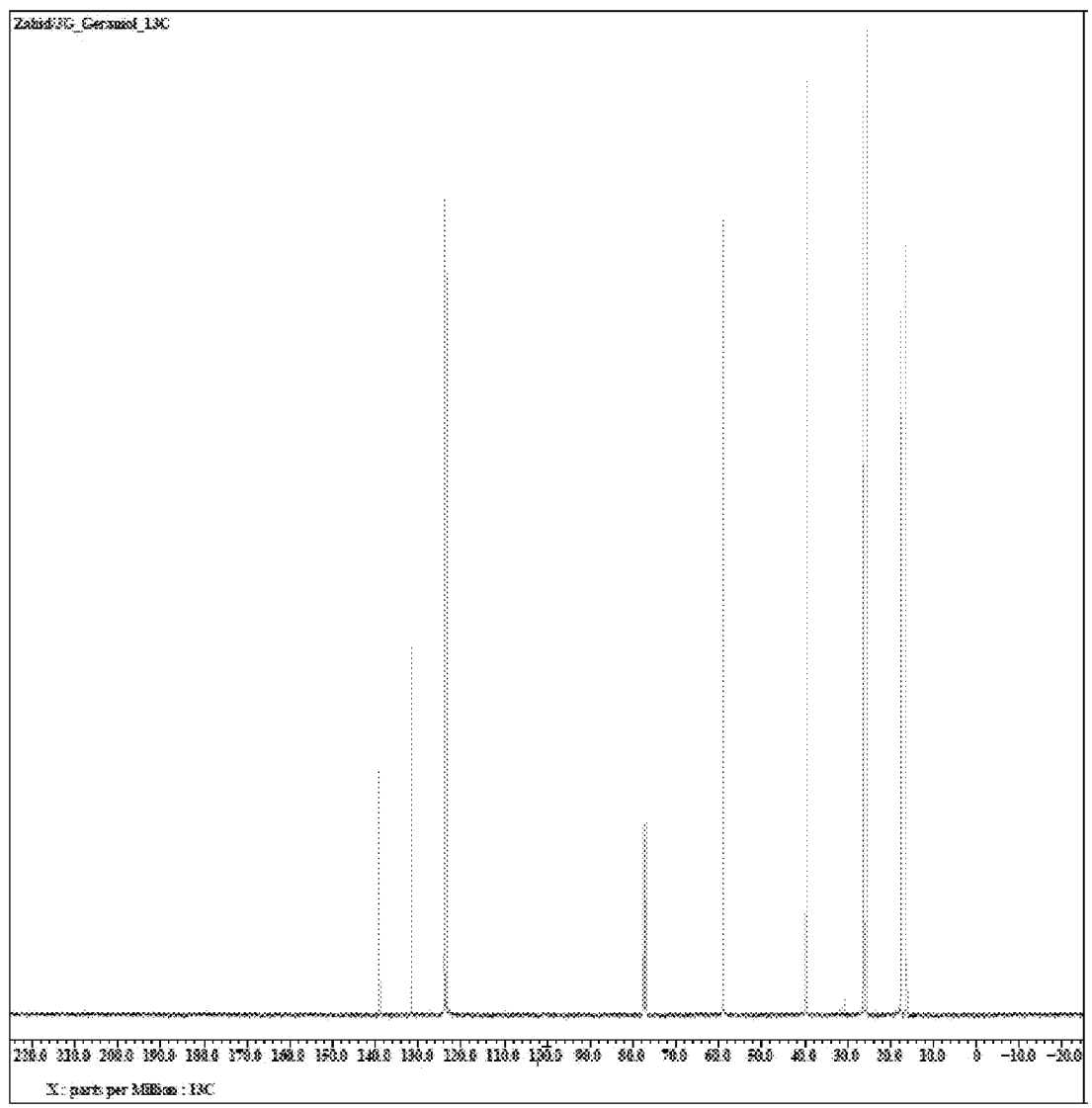

FIG. 10. A $^{13}$C nuclear magnetic resonance spectrum (NMR) of geraniol with $CDCl_3$ as the solvent.

Figure 11:
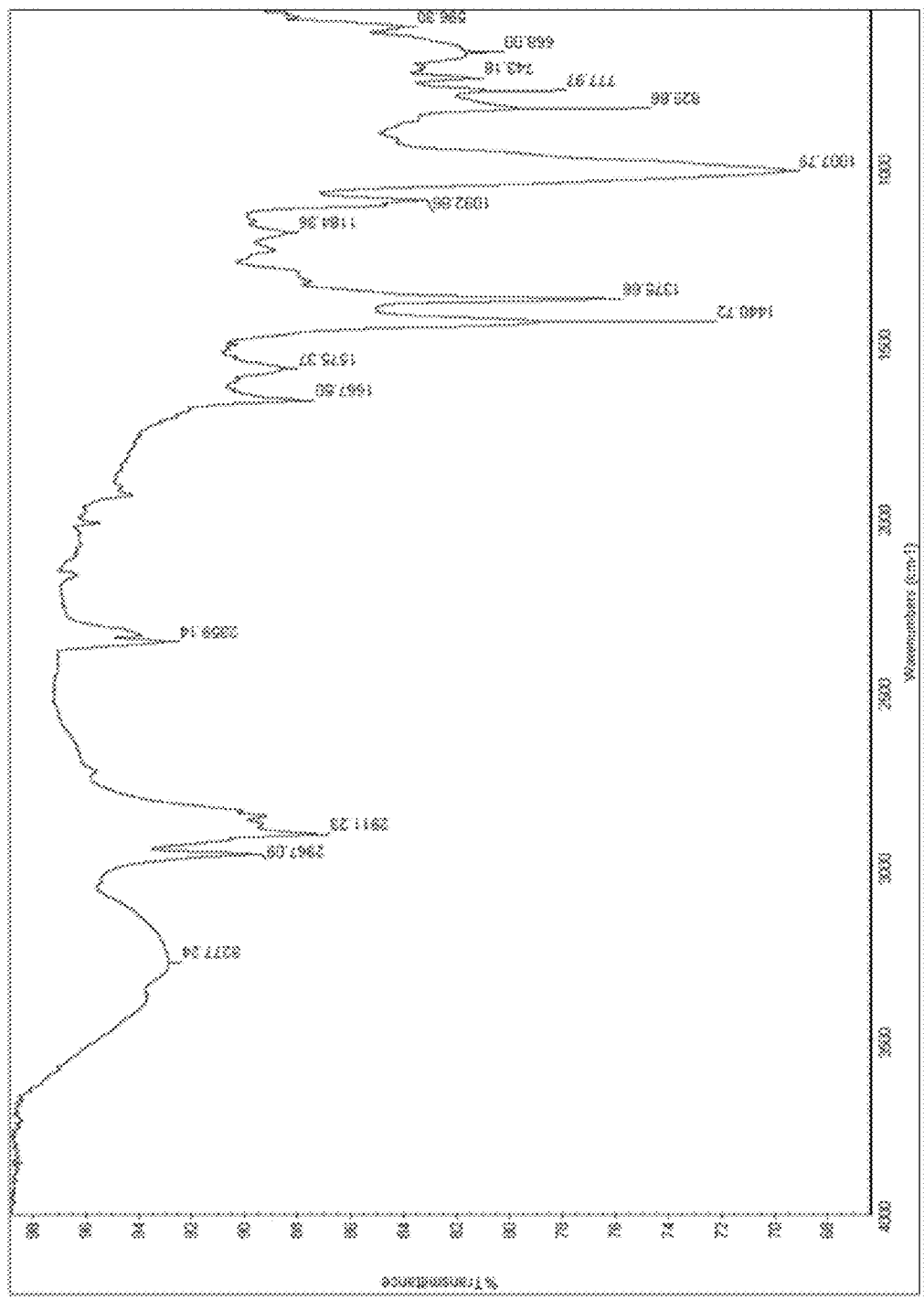

FIG. 11. A fourier transform infra-red spectrum (FTIR) of a product of the reaction between geraniol and potassium hydroxide (KOH).

Figure 12:
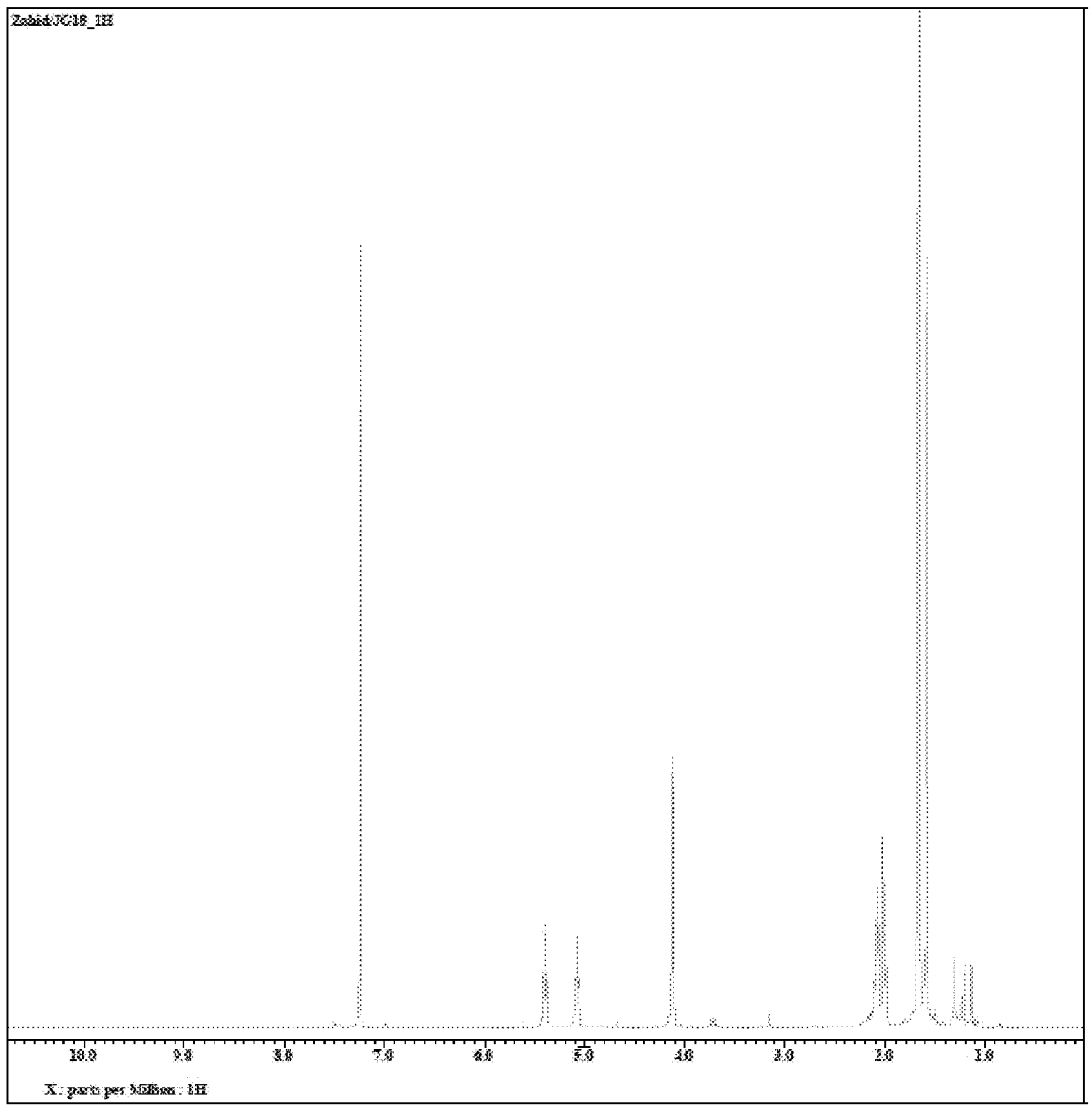

FIG. 12. A $^1$H nuclear magnetic resonance spectrum (NMR) of a product of the reaction between geraniol and potassium hydroxide (KOH) with $CDCl_3$ as the solvent.

Figure 13:
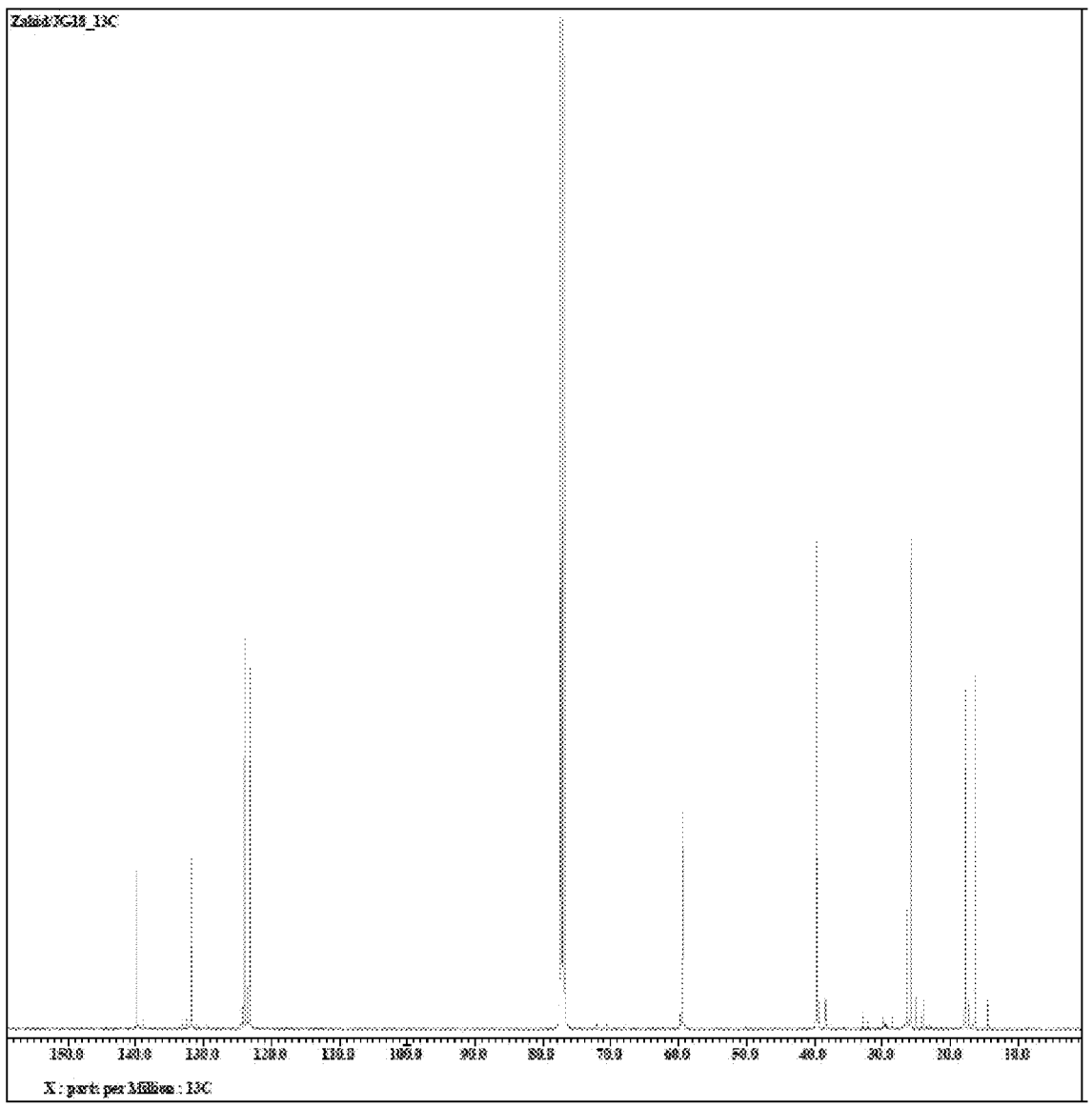

FIG. 13. A $^{13}$C nuclear magnetic resonance spectrum (NMR) of a product of the reaction between geraniol and potassium hydroxide (KOH) with $CDCl_3$ as the solvent.

Figure 14:
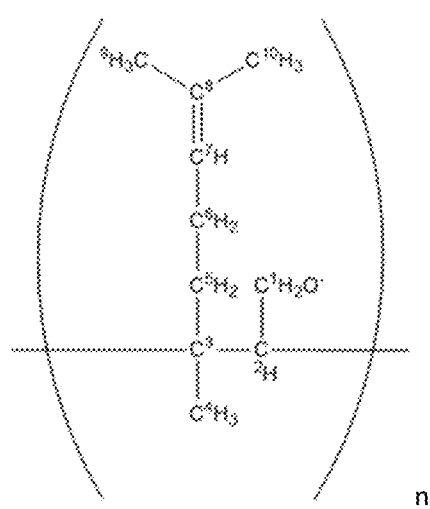

FIG. 14. A chemical structure of a proposed homopolymer of geraniol

Figure 15:
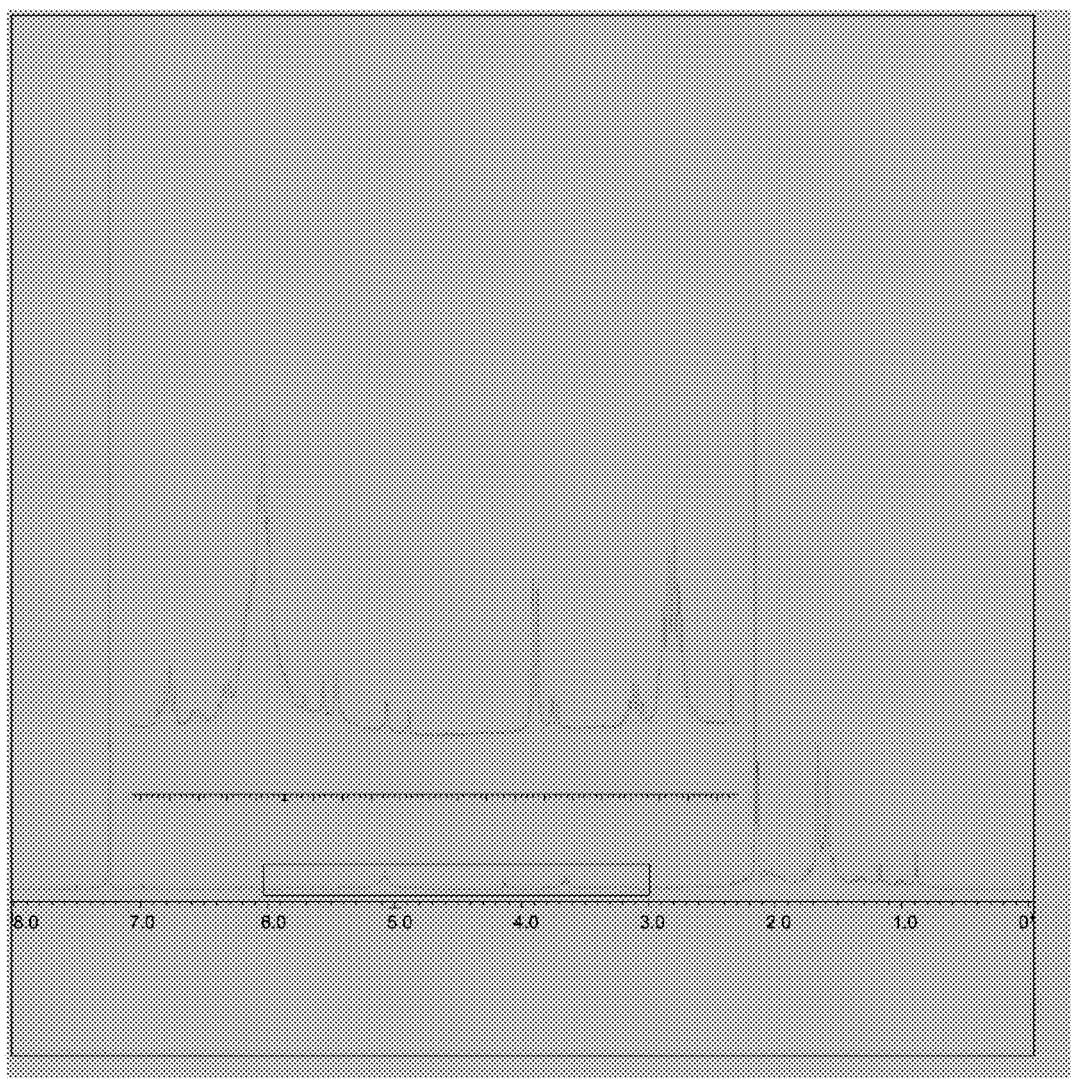

FIG. 15. A $^1$H nuclear magnetic resonance spectrum (NMR) of a geraniol homopolymer using AIBN as the initiator with $CDCl_3$ as the solvent.

Figure 16:
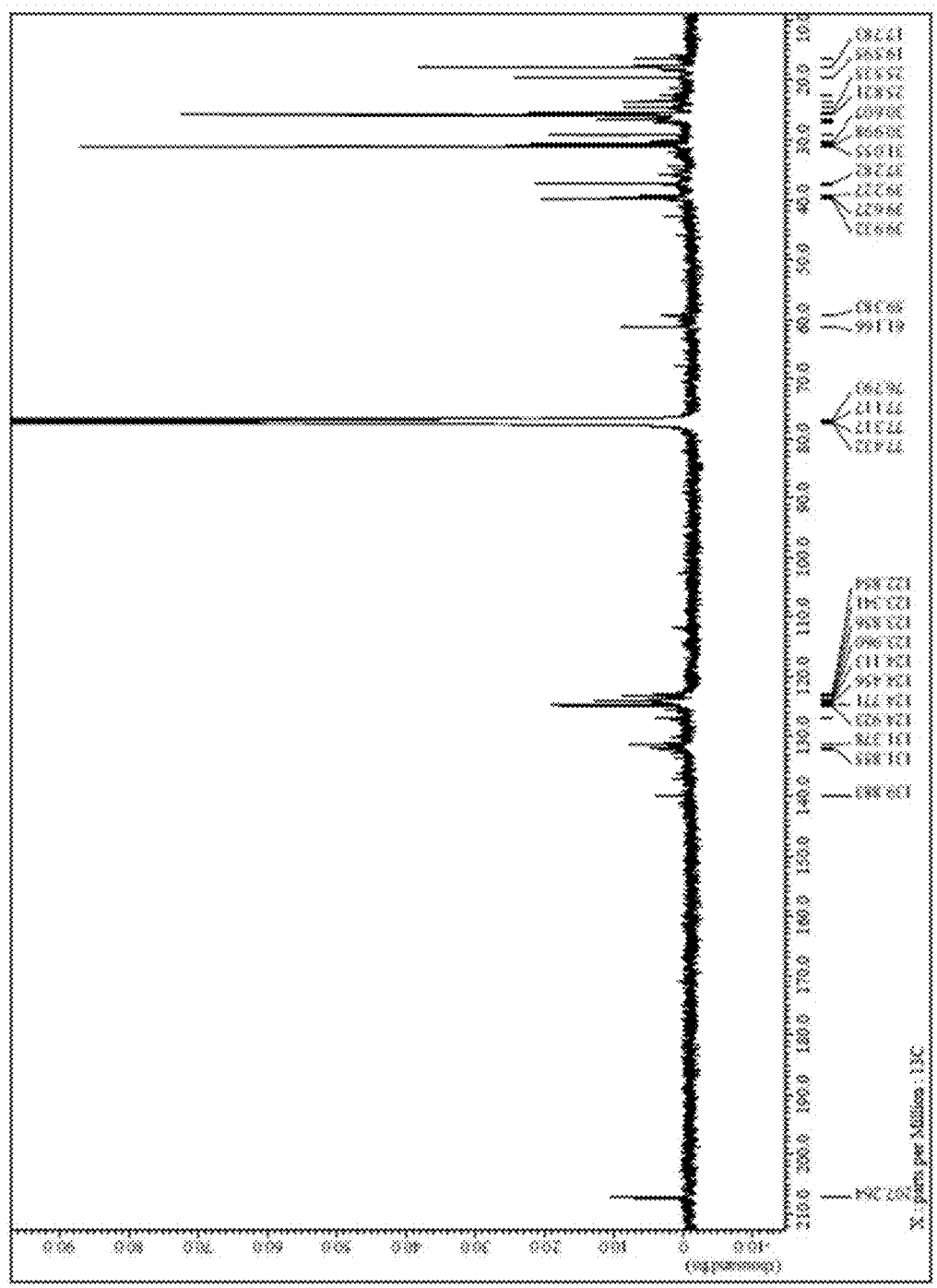

FIG. 16. A $^{13}$C nuclear magnetic resonance spectrum (NMR) of a geraniol homopolymer using AIBN as the initiator with $CDCl_3$ as the solvent.

Figure 17:
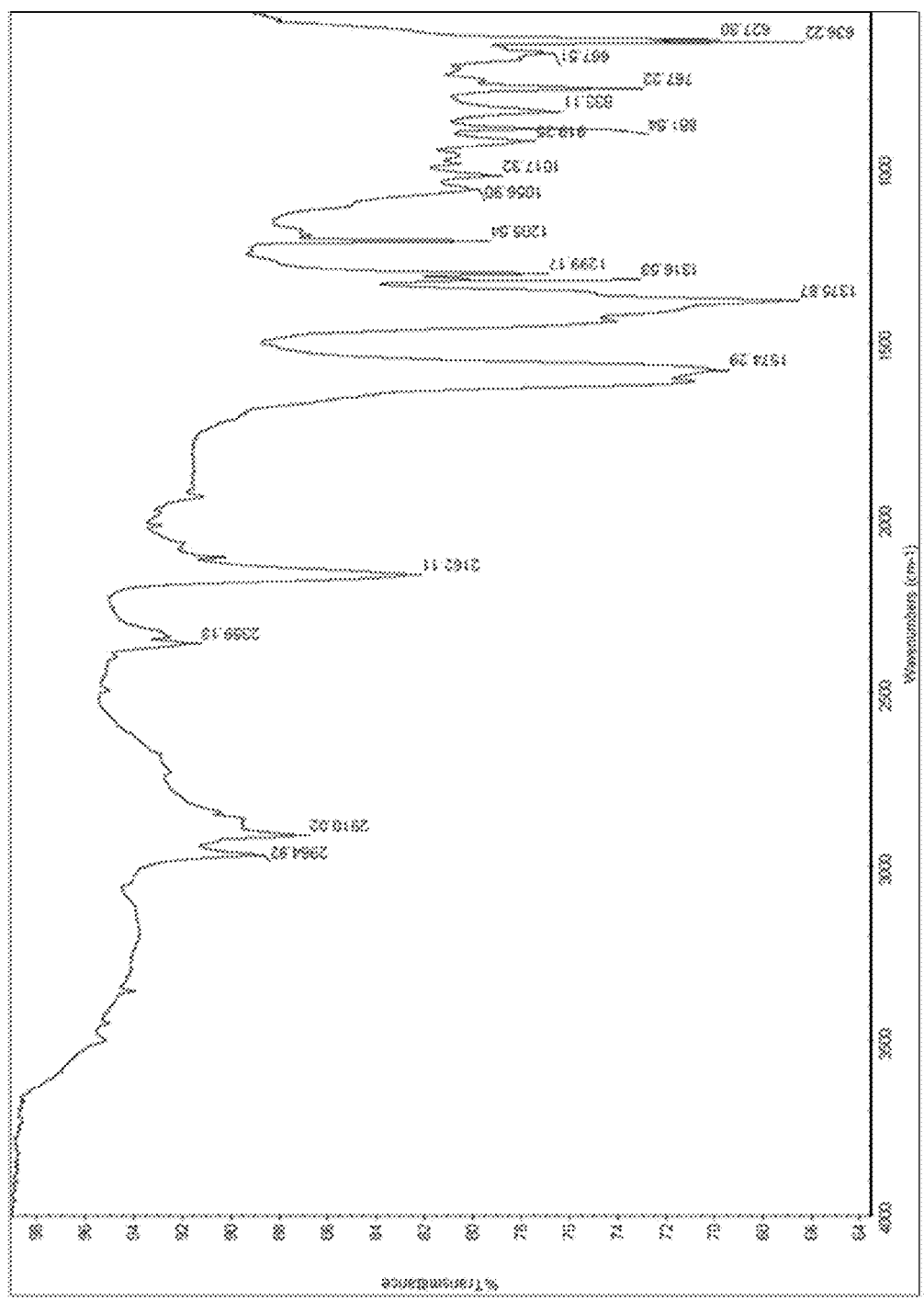

FIG. 17. A fourier transform infra-red spectrum (FTIR) of a geraniol homopolymer using AIBN as the initiator.

Figure 18:
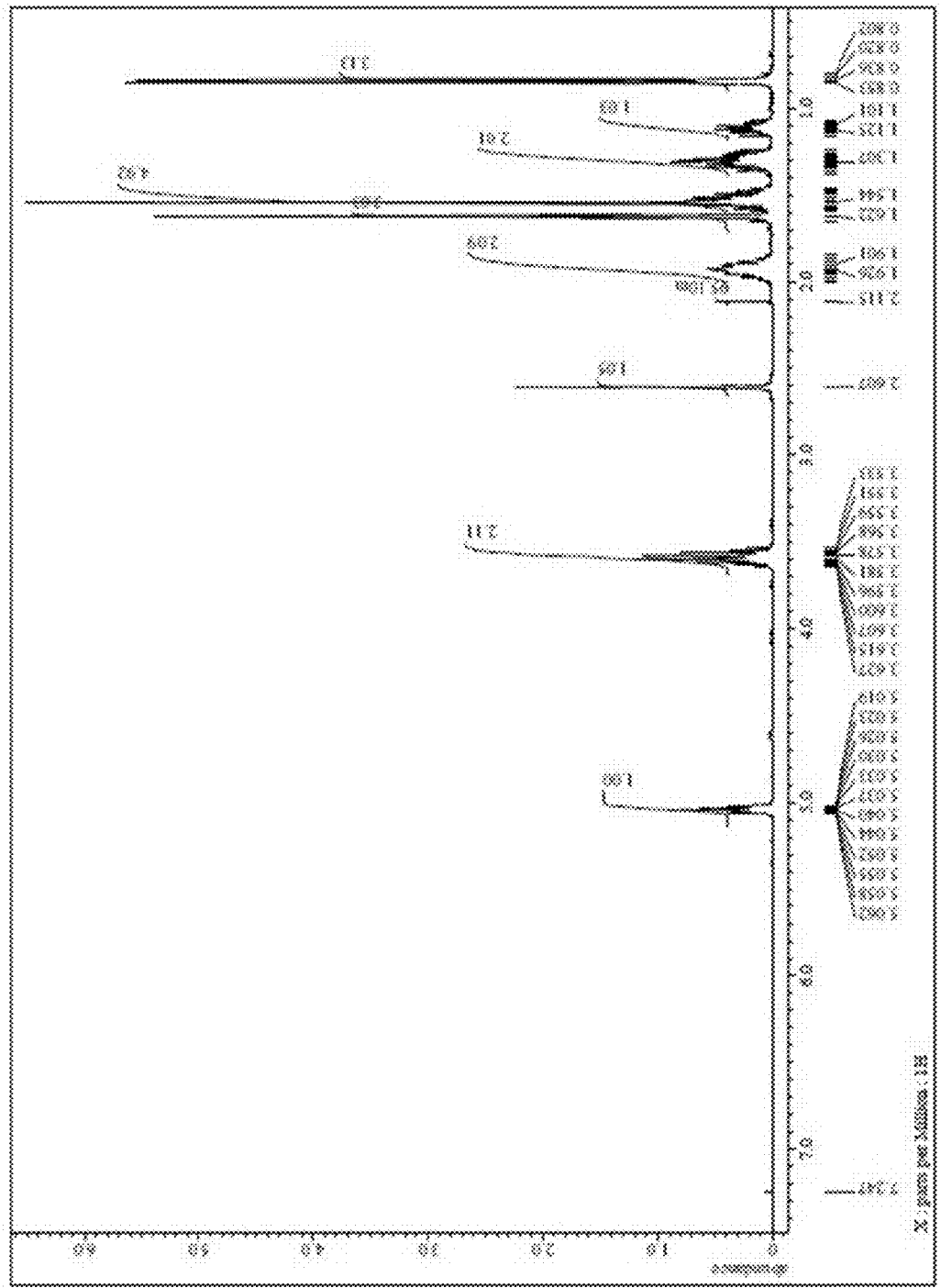

FIG. 18. A $^1$H nuclear magnetic resonance spectrum (NMR) of citronellol with $CDCl_3$ as the solvent.

Figure 19:
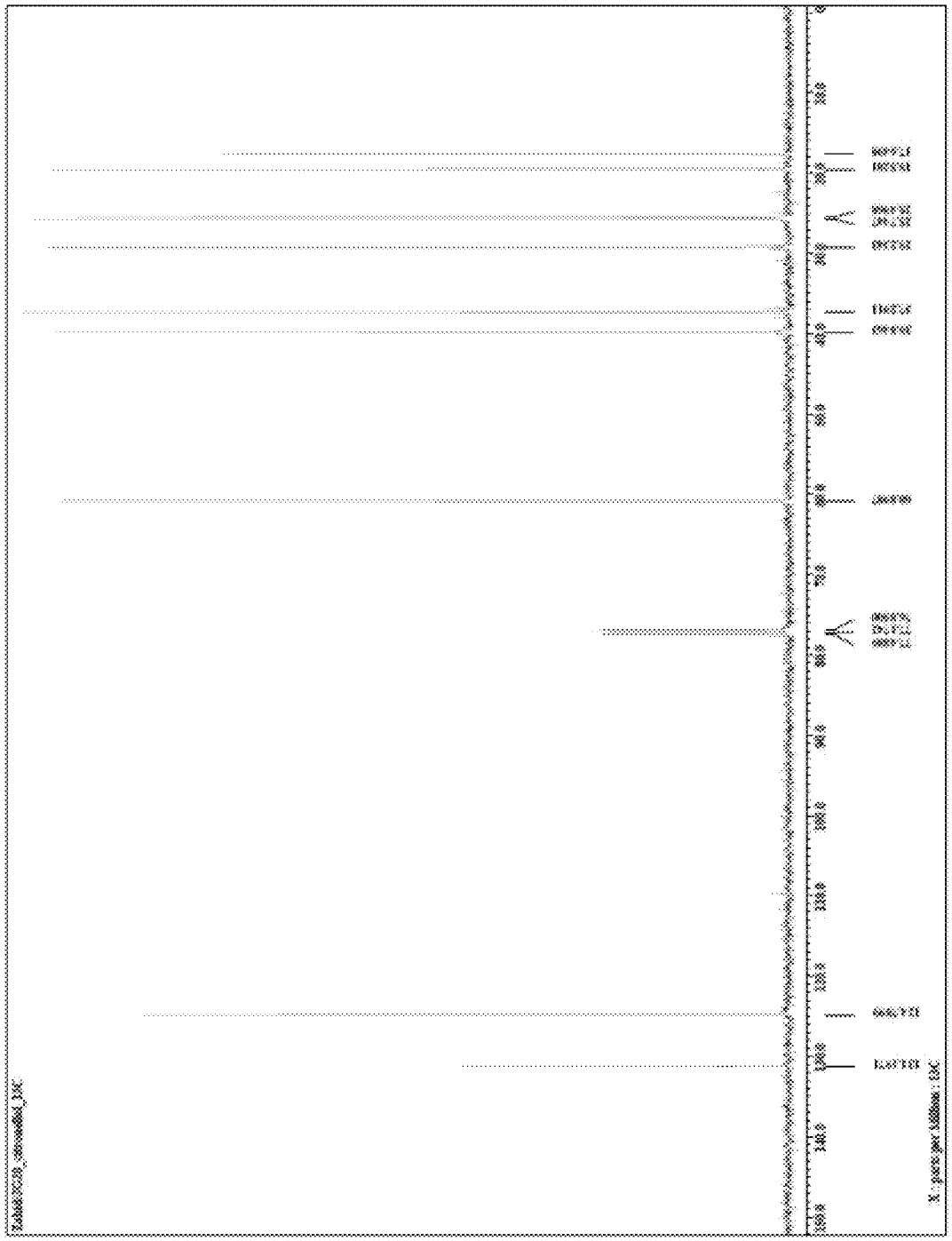

FIG. 19. A $^{13}$C nuclear magnetic resonance spectrum (NMR) of citronellol with $CDCl_3$ as the solvent.

Figure 20:
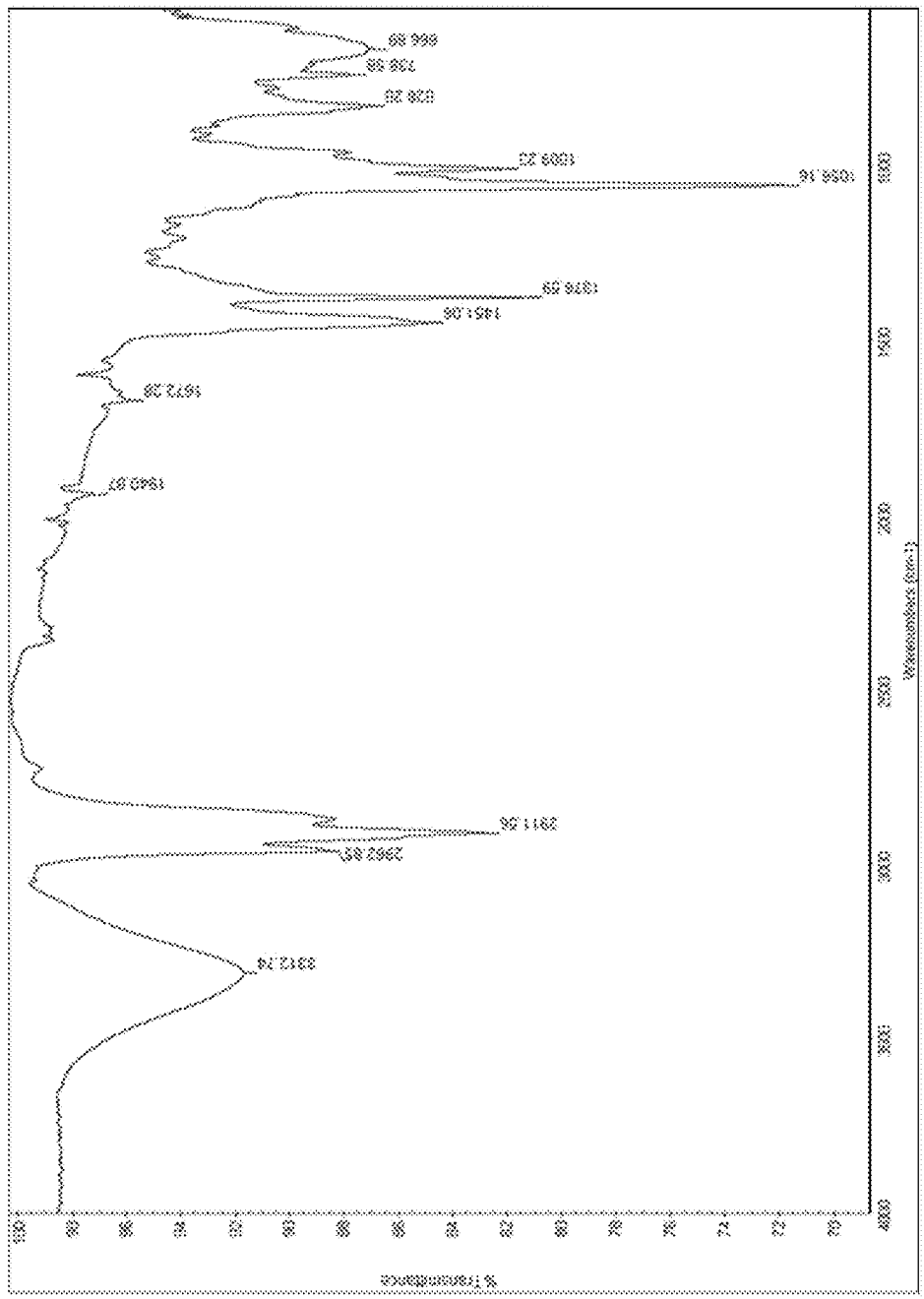

FIG. 20. A fourier transform infra-red spectrum (FTIR) of citronellol.

Figure 21:
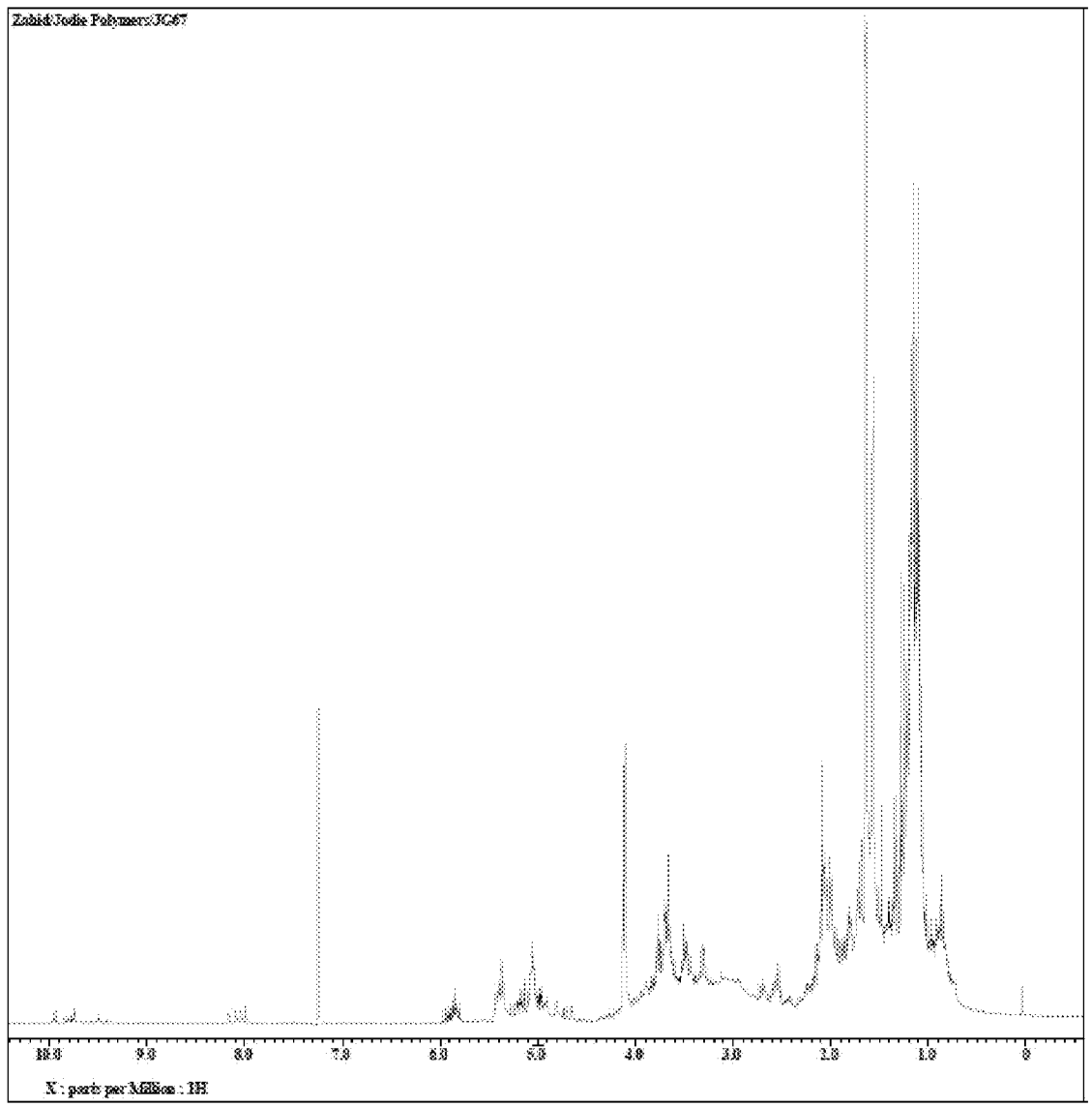

FIG. 21. A $^1$H nuclear magnetic resonance spectrum (NMR) of a geraniol homopolymer using hydrogen peroxide as the initiator with $CDCl_3$ as the solvent.

Figure 22:
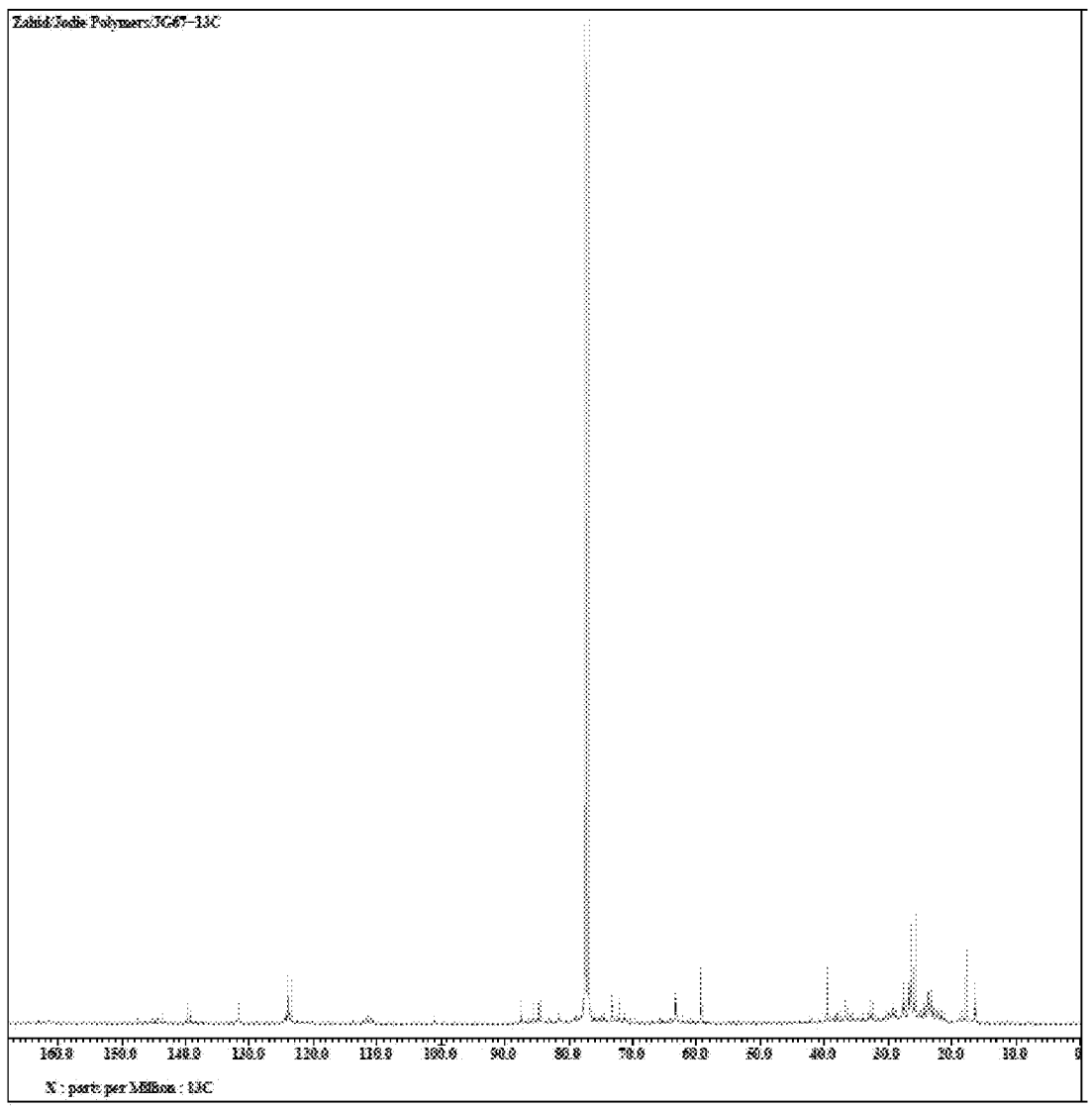

FIG. 22. A $^{13}$C nuclear magnetic resonance spectrum (NMR) of a geraniol homopolymer using hydrogen peroxide as the initiator with $CDCl_3$ as the solvent.

Figure 23:
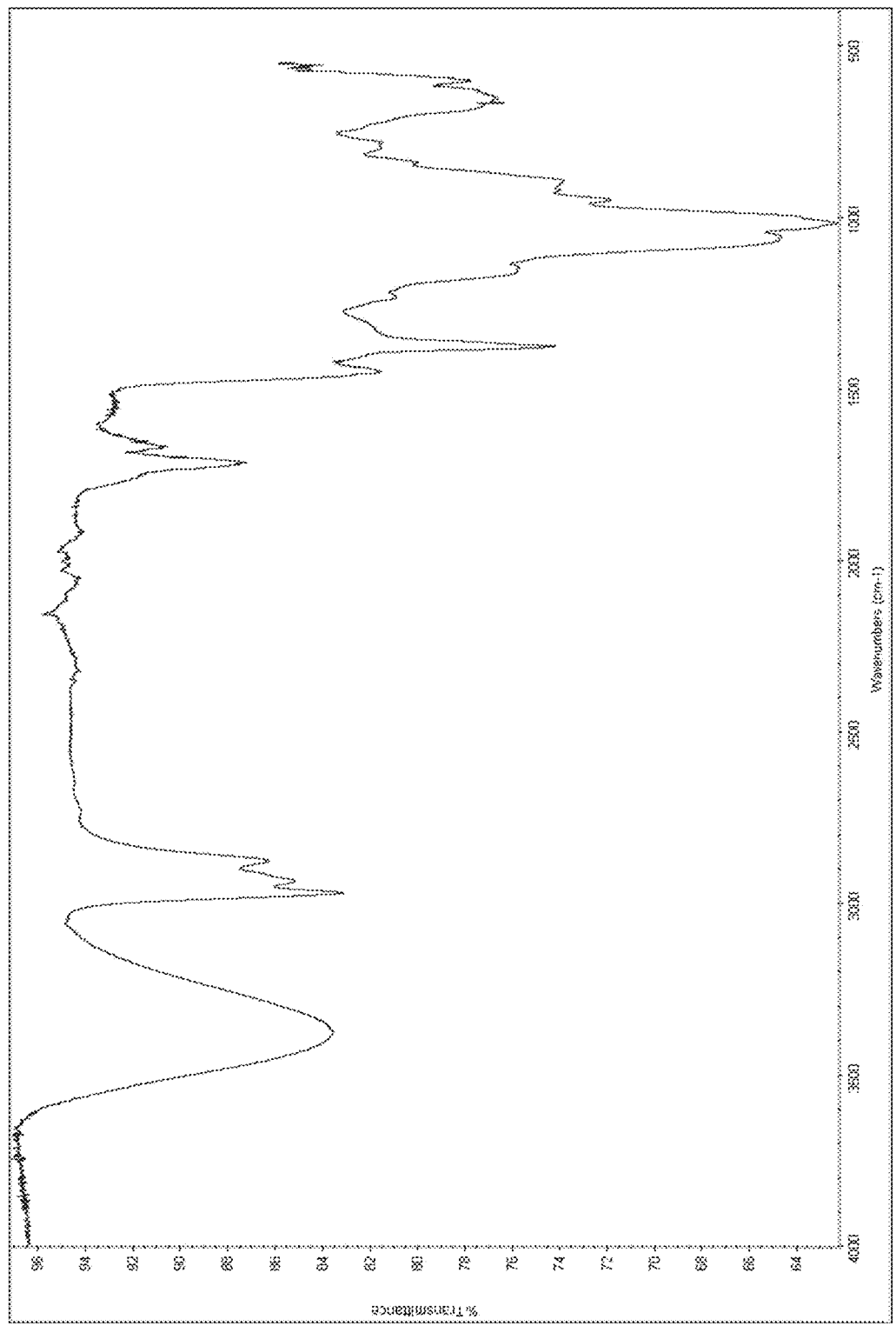

FIG. 23. A fourier transform infra-red spectrum (FTIR) of the geraniol homopolymer using hydrogen peroxide as the initiator.

Figure 24:
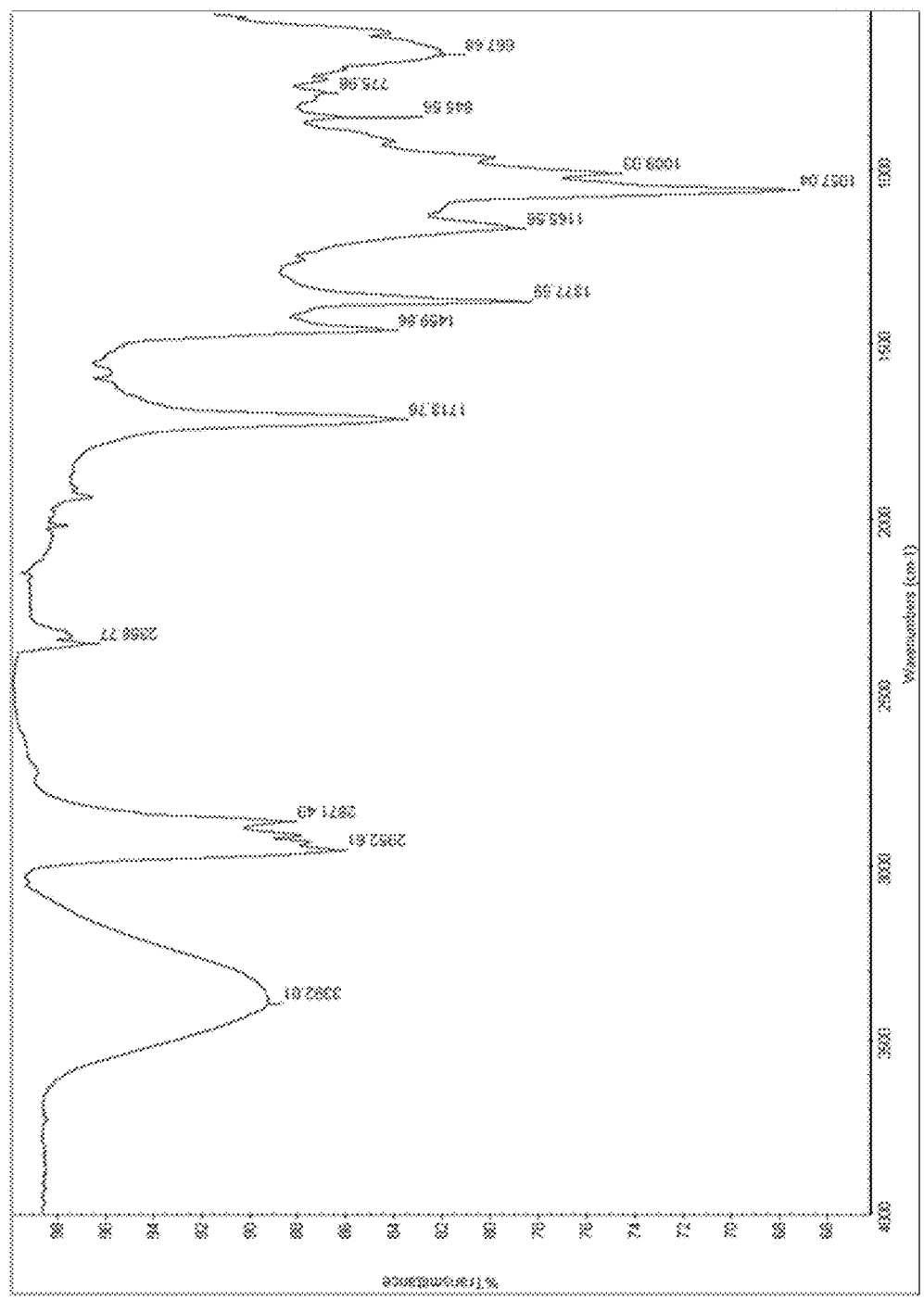

FIG. 24. A fourier transform infra-red spectrum (FTIR) of a citronellol homopolymer.

Figure 25:
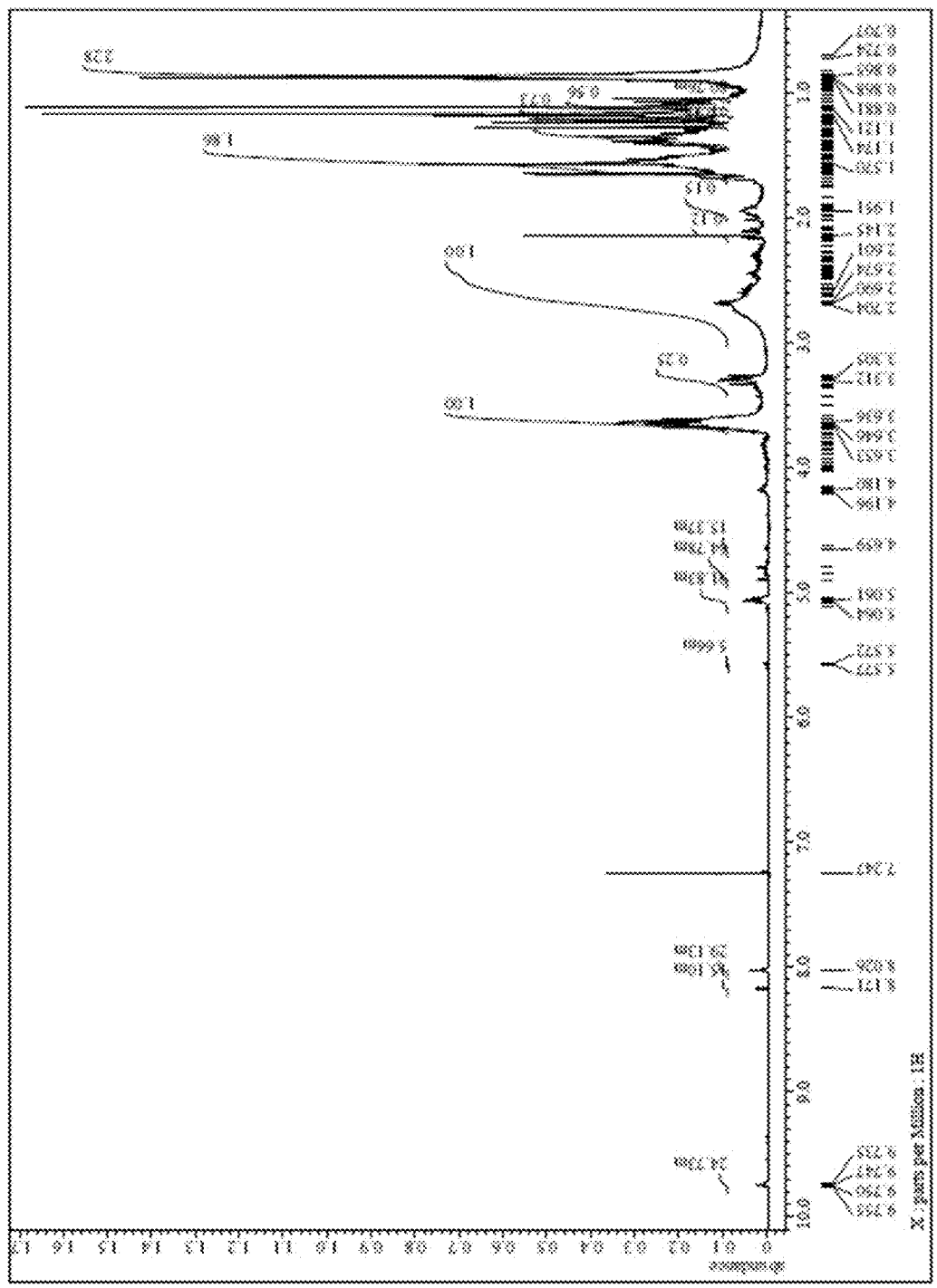

FIG. 25. A $^1$H nuclear magnetic resonance spectrum (NMR) of a citronellol homopolymer with $CDCl_3$ as the solvent.

Figure 26:
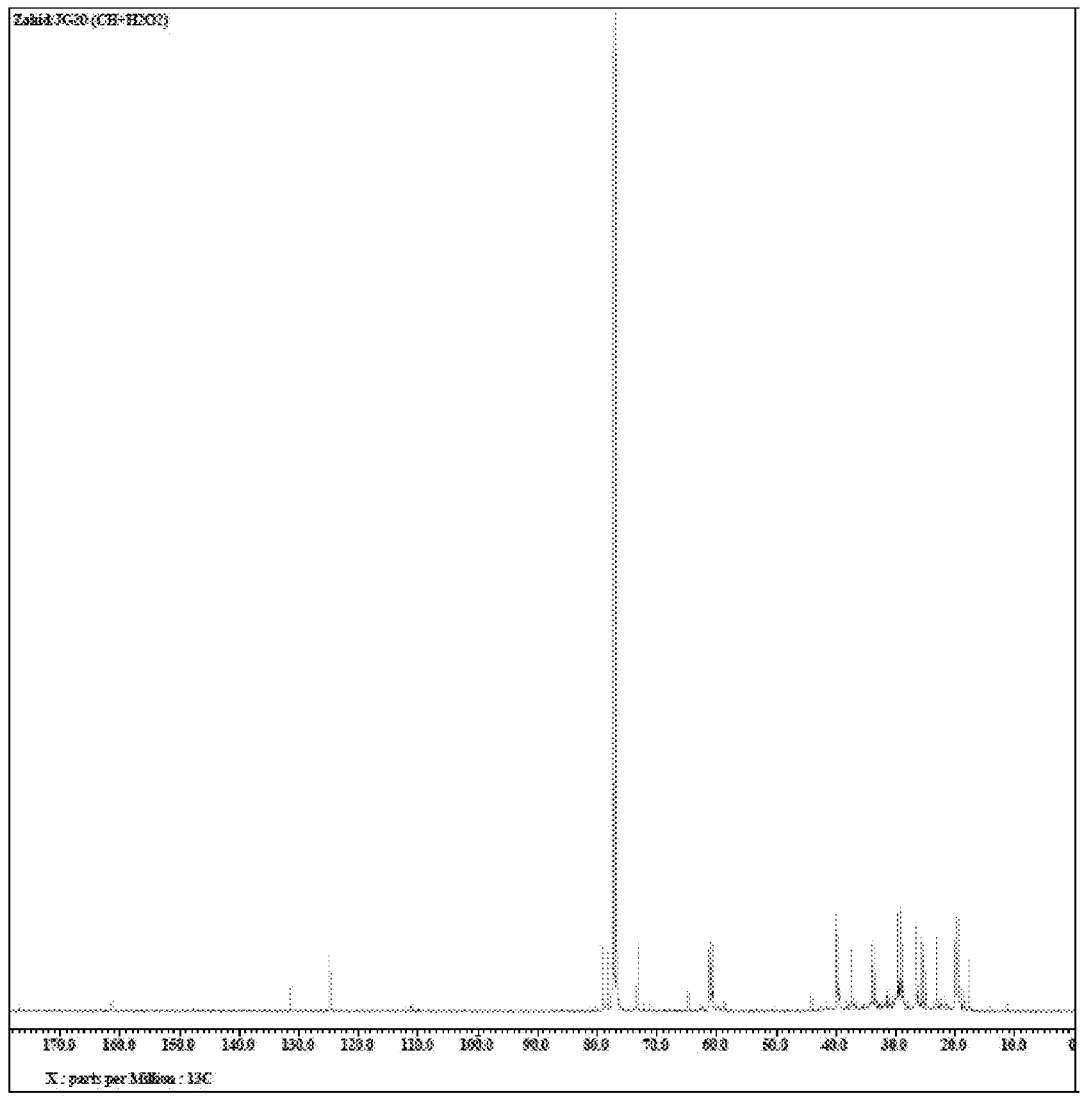

FIG. 26. A $^{13}$C nuclear magnetic resonance spectrum (NMR) of the citronellol homopolymer with $CDCl_3$ as the solvent.

Figure 27:
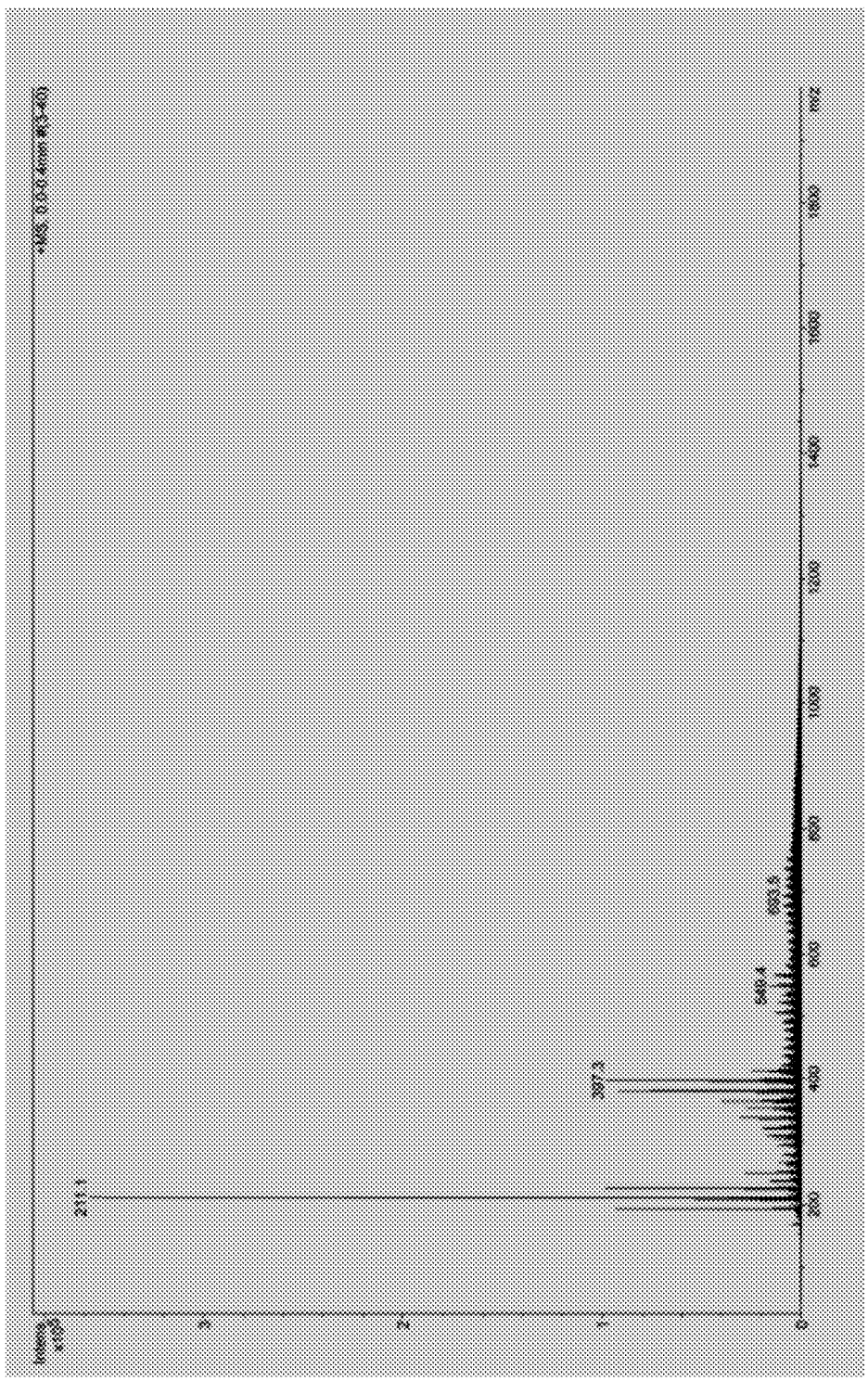

FIG. 27. A mass spectrum of a Linalool homopolymer.

Figure 28:
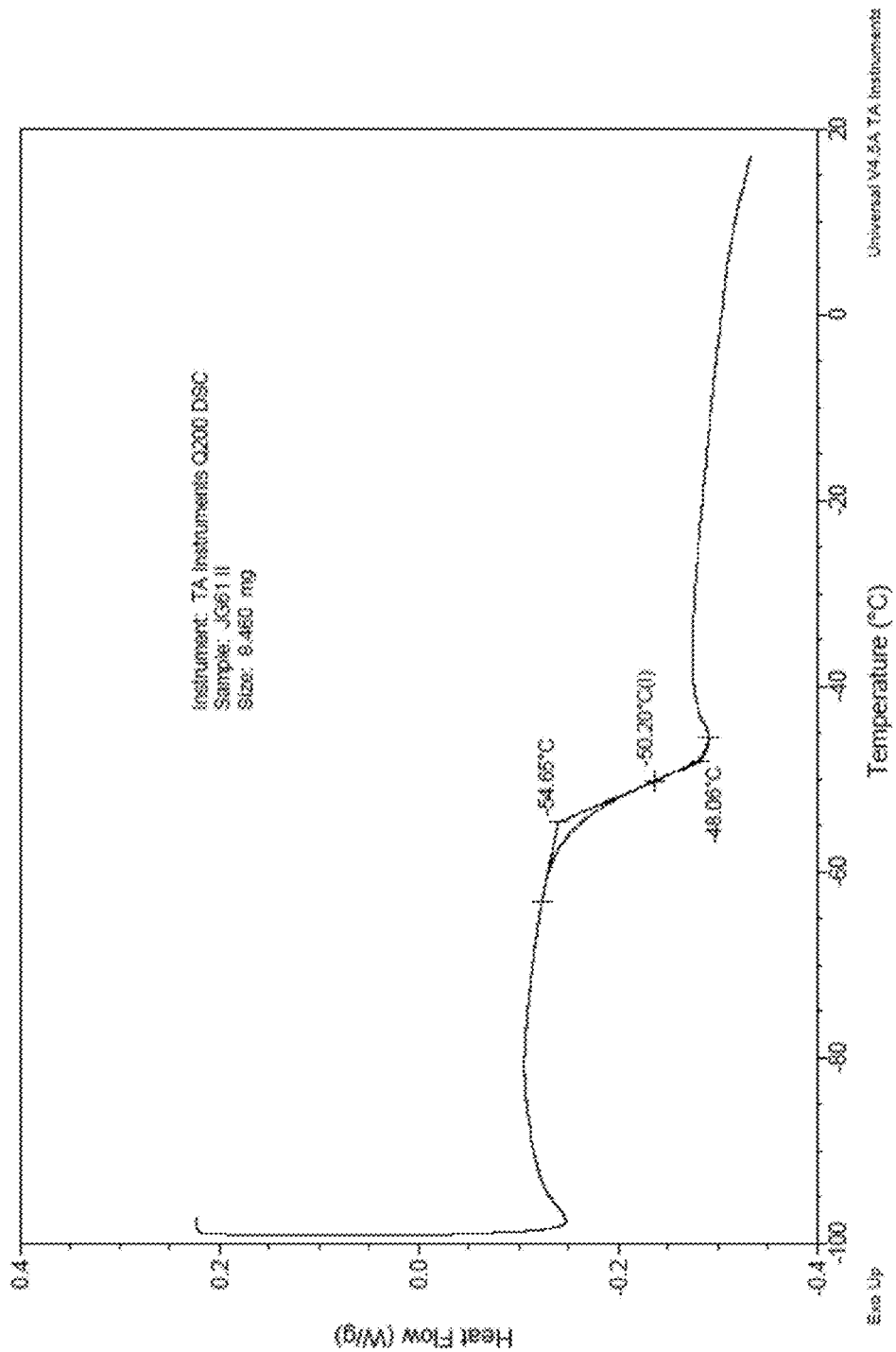

FIG. 28. A differential scanning calorimetry (DSC) plot of a citronellol homopolymer.

Figure 29:
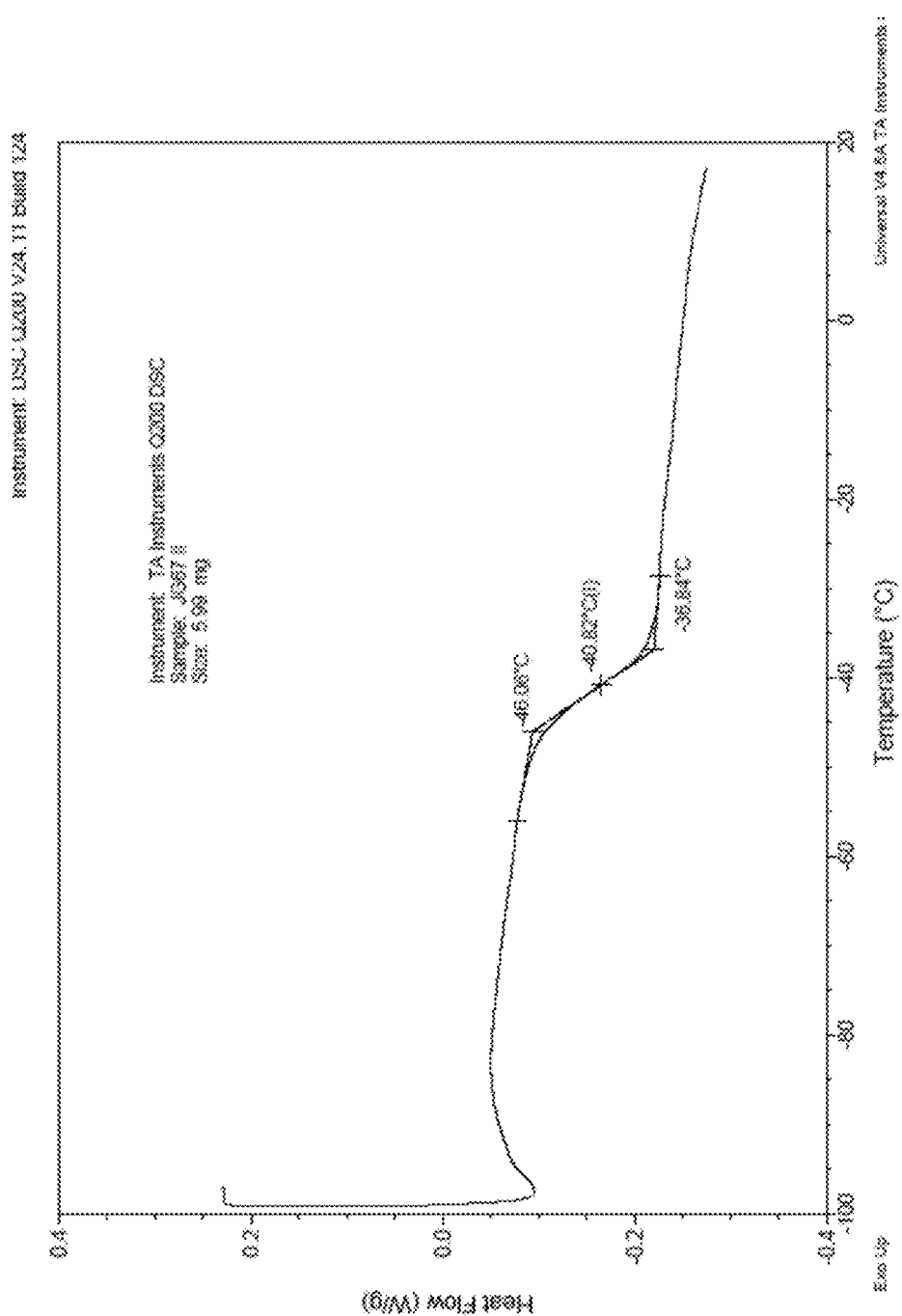

FIG. 29. A differential scanning calorimetry (DSC) plot of a geraniol homopolymer using hydrogen peroxide as the initiator.

Figure 30:
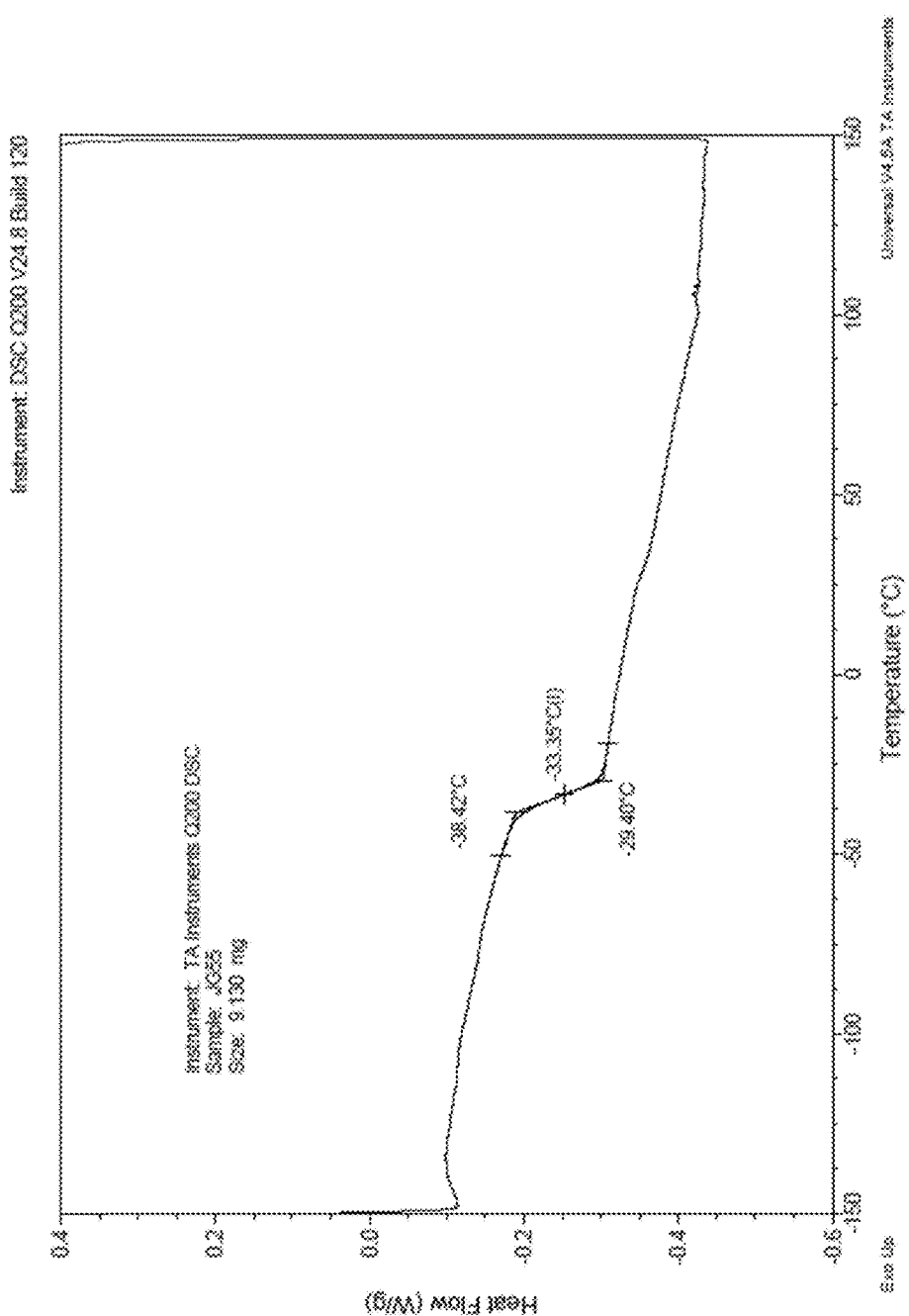

FIG. 30. A differential scanning calorimetry (DSC) plot of a linalool homopolymer.

Figure 31:
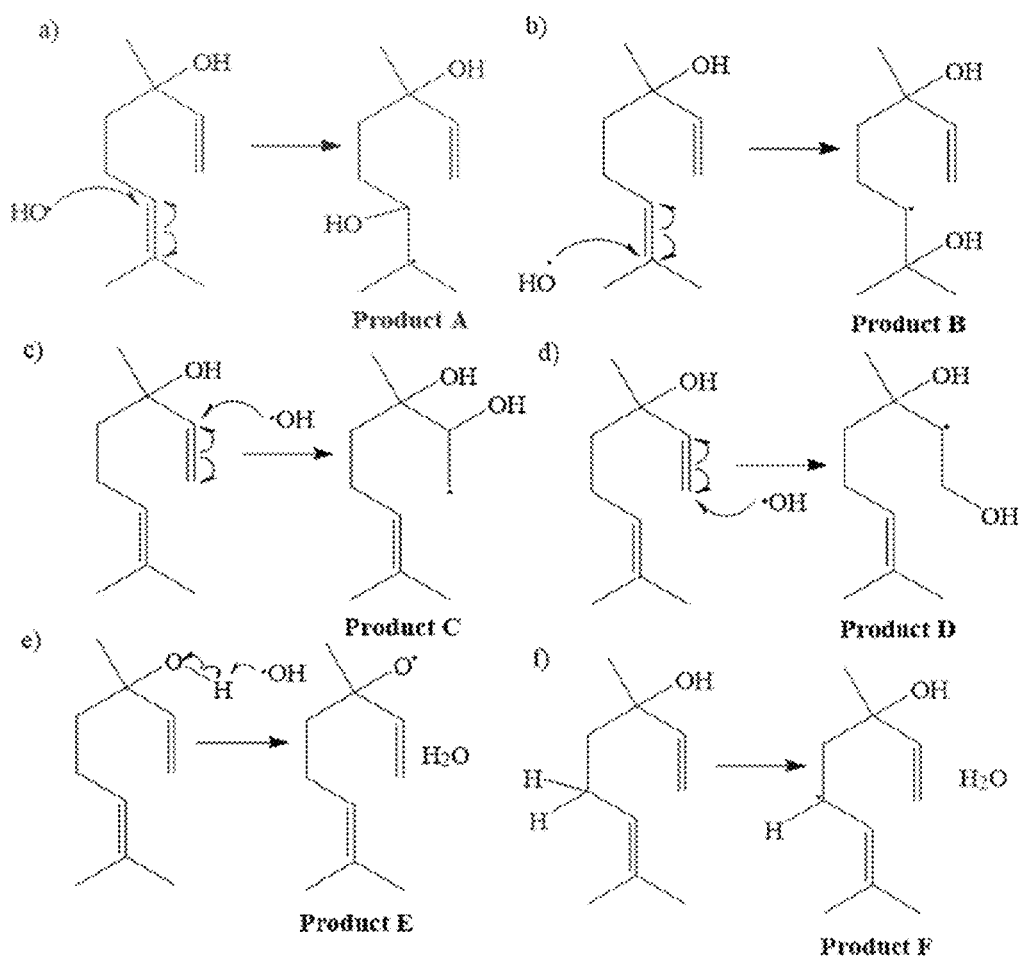

FIG. 31. A scheme of five possible reactions of a hydroxyl radical with linalool modelled computationally to determine site of polymerization.

DESCRIPTION OF VARIOUS EMBODIMENTS (I) Detailed Description

The present disclosure relates to the homopolyers of terpenoids containing at least one alcohol group and carbon-carbon double bond, polymerized using free radical polymerization. Detailed examples of the homopolymerization using the above technique on terpenoid monomers are presented below. Representative structures of the terpenoid homopolymers are shown below (I)

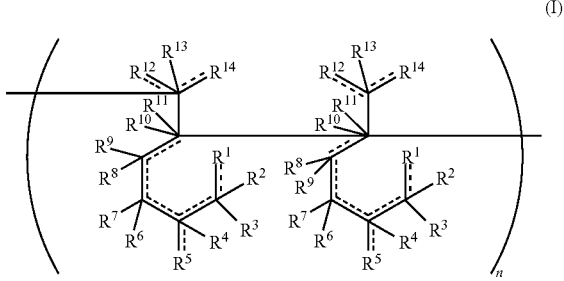

-continued

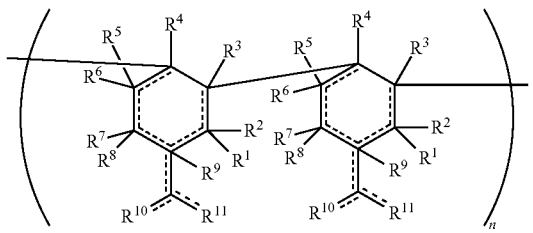

(II)

wherein the broken lines represent either a carbon-carbon single or double bond, with at least one carbon double bond being present in the monomer, which during polymerization is incorporated into the polymer backbone, $R^1$ to $R^{14}$ are independently or simultaneously H, halo, $(C_1-C_{24})$-alkyl, $(C_2-C_{24})$-alkenyl, $(C_2-C_{24})$-alkynyl, $(C_6-C_{14})$-aryl or $(C_5-C_{14})$-heteroaryl, wherein the latter five groups are optionally substituted and the optional substituents are chosen from one or more of halogen, —OH, $(C_1-C_6)$-alkyl, $(C_1-C_6)$-alkoxy, thionyl, nitro, amino (—$NH_2$), $(C_6-C_{14})$-aryl, $(C_5-C_{14})$-heteroaryl, phosphate (—$PO_4$), phosphoryl (—$PO_3$), and at least one of $R^1$-$R^{14}$ contains at least one —OH groups, and n is an integer between 1 and about 10,000.

In one embodiment, n is an integer between about 5 and about 1,000.

In one embodiment, n is an integer between about 5 and about 15.

In another embodiment, the polymers have the structure

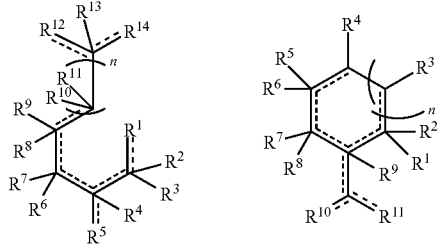

Terpenoids, or isoprenoids comprise a large class of organic chemicals similar to terpenes but with added oxygen functional group(s), consisting of 5 carbon isoprenene units, assembled and modified in numerous ways. The terpenoids of this disclosure include but are not restricted to acylic, and cyclic terpenoids, poly-cyclic terpenoids, terpenoids consisting of between 1 to 8 linked isoprene subunits and their derivatives provided they contain at least one alkene functionality and at least one hydroxyl (OH) functionality.

In one embodiment, the terpenoid monomers of the present disclosure are acyclic terpenoids of general structure

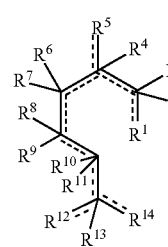

wherein the broken lines represent either a carbon-carbon single or double bond, with at least one carbon double bond being present in the structure, $R^1$ to $R^{14}$ are independently or simultaneously H, halo, $(C_1-C_{24})$-alkyl, $(C_2-C_{24})$-alkenyl, $(C_2-C_{24})$-alkynyl, $(C_6-C_{14})$-aryl or $(C_5-C_{14})$-heteroaryl, wherein the optional substituents are chosen from one or more of halogen, —OH, $(C_1-C_6)$-alkyl, $(C_1-C_6)$-alkoxy, thionyl, nitro, amino (—$NH_2$), $(C_6-C_{14})$-aryl, $(C_5-C_{14})$-heteroaryl, phosphate (—$PO_4$), phosphoryl (—$PO_3$), and at least one of $R^1$-$R^{14}$ contains at least one —OH groups In another embodiment the terpenoid monomers of the present disclosure are cyclic terpenoids of the general structure

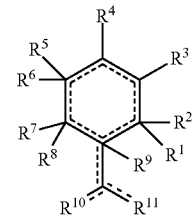

wherein the broken lines represent either a carbon-carbon single or double bond, with at least one carbon double bond being present in the structure, $R^1$ to $R^{14}$ are independently or simultaneously H, halo, $(C_1-C_{24})$-alkyl, $(C_2-C_{24})$-alkenyl, $(C_2-C_{24})$-alkynyl, $(C_6-C_{14})$-aryl or $(C_5-C_{14})$-heteroaryl, wherein the latter five groups are optionally substituted and the optional substituents are chosen from one or more of halogen, —OH, $(C_1-C_6)$-alkyl, $(C_1-C_6)$-alkoxy, thionyl, nitro, amino (—$NH_2$), $(C_6-C_{14})$-aryl, $(C_5-C_{14})$-heteroaryl, phosphate (—$PO_4$), phosphoryl (—$PO_3$), and at least one of $R^1$-$R^{14}$ contains at least one —OH groups.

In one embodiment, $R^1$ to $R^{14}$ are independently or simultaneously H, halo, $(C_1-C_{10})$-alkyl, $(C_2-C_{10})$-alkenyl, $(C_2-C_{10})$-alkynyl, $(C_6-C_{10})$-aryl or $(C_5-C_{10})$-heteroaryl. In another embodiment, $R^1$ to $R^{14}$ are independently or simultaneously H, halo, $(C_1-C_6)$-alkyl, $(C_2-C_6)$-alkenyl, $(C_2-C_6)$-alkynyl, $(C_6)$-aryl or $(C_5-C_6)$-heteroaryl. In another embodiment, $R^1$ to $R^{14}$ are independently or simultaneously H or $(C_1-C_6)$-alkyl, In another embodiment the terpenoid monomer of the present disclosure is geraniol, citronellol, linalool, nerol, rhodinol, lasiol, trans nerolidol, cis nerolidol, having the structures

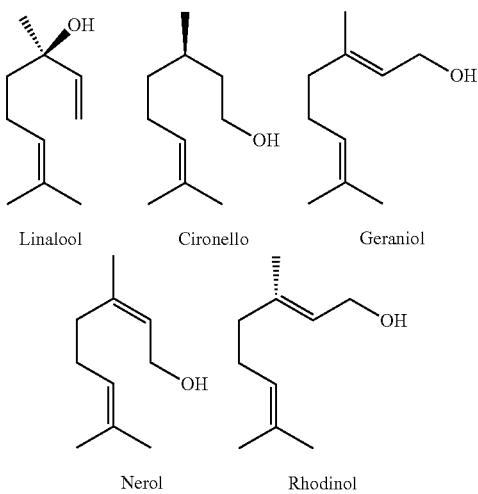

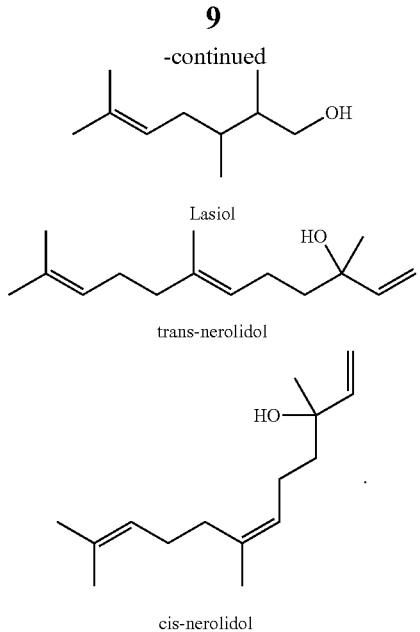

Lasiol trans-nerolidol cis-nerolidol

In another embodiment the terpenoid monomer of the present disclosure is terpineol and its isomers.

In another embodiment of the present disclosure the free radical initiator is hydrogen peroxide, an azo initiator, a halogen initiator, an organic peroxide initiator, an inorganic peroxide initiator, a hydroxyperoxy initiator, or a transition metal catalyst capable of generating radicals for polymerization.

In another embodiment of the present disclosure the polymerization is initiated thermally. In another embodiment polymerization is photoinitiated.

In another embodiment of the disclosure the polymerization reaction is conducted in a solvent. In another embodiment the polymerization reaction is conducted without the use of solvents.

In one embodiment of the current disclosure the terpenoid homopolymer of citronellol is synthesized. In another embodiment the terpenoid homopolymer of linalool is synthesized. In another embodiment the terpenoid homopolymer of geraniol is synthesized.

The present disclosure also includes uses of the terpenoid homopolymers, for example, the terpenoid homopolymers of the current disclosure are functional polyol pre-polymers, with applications including urethane polymerization. In another embodiment the terpenoid homopolymers are anti-microbial. In another embodiment, the terpenoid homopolymers are preservative materials. In another embodiment, the terpenoid homopolymers of the present disclosure are insecticide and pest control materials.

In another embodiment, the terpenoid homopolymers are therapeutic agents. In another embodiment the terpenoid homopolymers are organoleptic agents, and can be incorporated into cosmetic and consumer formulations. In another embodiment, the terpenoid homopolymers are incorporated into a finished consumer product or packaging material to impart antimicrobial or organoleptic properties to material. In another embodiment the terpenoid homopolymer forms a liquid antimicrobial coating by non-covalently bonding to the desired surface. In another embodiment, the terpenoid homopolymer is used as a film or surface coating material by chemical functionalization or reactions of the hydroxyl group with the surface. In another embodiment, the terpenoid homopolymers of present disclosure can act as renewable plastic materials.

(IV) Uses of the Disclosure

The polymers of this disclosure have many uses. For example, linalool and citronellol are known pest control agents and the polymers of the disclosure can be applied or sprayed as a diluted solution to control pests indoors.

In one embodiment, the terpenoid monomers are often used as scents in cosmetic formulations. As the polymers of the present disclosure are antimicrobial and retain the characteristic odors of the monomers, they can act as antimicrobial and scent additives to cosmetic formulations. For example, a lotion containing a 1% cross-linked viscosity modifier, 81% water, 5% cetearyl alcohol, 4% coconut oil, 1.5% linalool homopolymer, and 3% almond oil was made as a proof of concept demonstrating the ability to incorporate the polymers of this disclosure into consumer products.

In one embodiment, the terpenoid homopolymers of the present disclosure are liquid polyols, and can thus act as green, renewable based liquid pre-polymers for the synthesis of polyurethanes and urethane chemistry.

In one embodiment, the terpenoid monomers of the present disclosure are derived from food based sources and polymerized by hydrogen peroxide and can act as a natural organoleptic agent.

In one embodiment, the anti-microbial homopolymers of the present disclosure can also be added to packaging materials, and incorporated into various articles to impart anti-microbial activity to the finished product.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

(II) EXAMPLES

Example 1—Synthesis of Homopolymer of Linalool

Linalool (Sigma-Aldrich, 10.000 mL, 56.40 mmol) was heated to 110° C. under magnetic stirring in a reaction vessel, at which point hydrogen peroxide (Sigma-Aldrich, 10.00 mL of 30% weight in water) was added. The heat was left on for 80 minutes while the clear solution boiled and began to turn yellow then darken to orange/red. A viscous orange/red liquid polymer was collected. The polymers were then characterized by FTIR, NMR, viscosity computational methods and mass spectrometry. Where indicative of monomer presence in the product by NMR, the polymers were purified by vacuum distillation.

In other example synthesis of homopolymers of linalool, the ratio of initiator to monomer as expressed as a weight percent of the pure initiator to monomer was varied from a few weight percent to 50 weight percent. The resulting homopolymers possessed different viscosities and molecular weights.

Example 2—Synthesis of Homopolymer of Geraniol

Geraniol (Sigma-Aldrich, 10.000 mL, 56.40 mmol) was heated to 110° C. under magnetic stirring in a reaction vessel, at which point hydrogen peroxide (Sigma-Aldrich, 10.00 mL of 30% weight in water) was added. The heat was left on for 80 minutes while the clear solution boiled and began to turn yellow then darken to orange/red. The maximum temperature in the reaction vessel reached 204 Celsius during the course of the reaction. A viscous orange/red liquid polymer was collected. The polymers were then characterized by FTIR, NMR, viscosity and mass spectrometry. Where indicative of monomer presence in the product by NMR, the polymers were purified by vacuum distillation.

In other example synthesis of homopolymers of geraniol, the ratio of initiator to monomer as expressed as a weight percent of the pure initiator to monomer was varied from a few weight percent to 50 weight percent. The resulting homopolymers possessed different viscosities and molecular weights.

Geraniol was also polymerized through the reversible deprotonation of the hydroxyl group followed by free radical polymerization across the carbon double bond. In this method, Potassium hydroxide (0.29 g, 5.17 mmol) was dissolved in distilled water (0.500 mL) to which geraniol (1.000 mL, 5.64 mmol) was added. The solution was heated and stirred. When the temperature reached 80° C., 2,2'-Azobis(2-methylpropionitrile) (0.10 g, 10% weight) was added to the yellow solution. The heat was left on and the solution darkens to orange then dark red/orange. After 26 minutes the heat is turned off (maximum temperature reached is 160° C.). The resulting final product is a brown solid, and can be re-protonated by reacting it with an acid.

Similarly, other reactants well known in the literature can be used to deprotonate the hydroxyl group prior to polymerization. Likewise the hydroxyl group can also be protected by reacting it with silyl ethers, or other well-known protecting groups prior to polymerization.

Finally, to examine the reactivity of geraniol with the base a second control sample containing potassium hydroxide (0.29 g, 5.17 mmol) was dissolved in distilled water (0.500 mL) to which geraniol (1.000 mL, 5.64 mmol) was added. The solution was heated and stirred. With the heat the solution turns yellow then orange and continues to darken to a final blood red/orange solution and the heat is turned off (maximum temperature reached is 180° C.). The final product is a light brown liquid.

The polymerized geraniol, as well as the de-protonated control was analyzed by FTIR, and NMR spectroscopy to demonstrate polymerization of the sample.

Example 3—Synthesis of Homopolymer of Citronellol

Citronellol (2.000 mL, 10.94 mmol) was heated under magnetic stirring in a reaction vessel to 110° C. at which point hydrogen peroxide (0.667 mL 30% weight, 10% weight) was added. The solution is heated over 34 minutes with no visible changes and reaches a temperature height of 160° C. At this point more hydrogen peroxide was added (1.000 mL 30% weight). Heat was left on for another 28 minutes as the solution turns yellow and the temperature reaches a maximum of 175° C. At his point the heat was turned off and the viscous yellow solution was collected and analysed.

Citronellol was also polymerized through the reversible deprotonation of the hydroxyl group followed by free radical polymerization across the carbon double bond. In this method, Potassium hydroxide (0.3 g, 5.17 mmol) was dissolved in distilled water (0.500 mL) to which citronellol (1.000 mL, 5.48 mmol) was added. The solution was heated and stirred. When the temperature reached 80° C., 2,2'-Azobis(2-methylpropionitrile) (0.10 g, 10% weight) was added to the yellow solution. The heat was left on and the solution darkens to yellow/orange then dark orange/brown color. After 26 minutes the heat is turned off (maximum temperature reached is 130° C.). The resulting final product can be re-protonated by reacting it with an acid.

Similarly, other reactants well known in the literature can be used to deprotonate the hydroxyl group prior to polymerization. Likewise the hydroxyl group can also be protected by reacting it with silyl ethers, or other well-known protecting groups prior to polymerization.

Finally, to examine the reactivity of citronellol with the base a second control sample containing potassium hydroxide (0.3 g, 5.17 mmol) was dissolved in distilled water (0.500 mL) to which citronellol (1.000 mL, 5.48 mmol) was added. The solution was heated and stirred. With the heat the solution turns yellow then orange and the heat is turned off (maximum temperature reached is 180° C.). The final product is a dark orange liquid.

Example 4—Characterization of the Homopolymers by Nuclear Magnetic Resonance (NMR) Spectroscopy Nuclear Magnetic Resonance (NMR) Spectroscopy. $^1$H-NMR and $^{13}$C-NMR were recorded by JEOL ECS-400 MHz NMR Spectrometer at ambient temperature with deuterated chloroform purchased from Sigma-Aldrich and used as received. Data processing was performed using Delta NMR Processing and Control Software v5.0.4.

i. Linalool Homopolymers

The $^1$H-NMR and $^{13}$C-NMR of linalool is presented in FIGS. 1, and 2 respectively. The $^1$H-NMR and $^{13}$C-NMR of the linalool homopolymer is shown in FIGS. 5 and 6 respectively. The key peaks identified for the $^1$H NMR of the polymer are (CDCl$_3$, 400 MHz): δ 5.97-5.72 (m, 1H, $H^B$), 5.30-4.81 (m, 2H, $H^A$ and $H^{A'}$), 4.20-2.88 (m, 11H, O—H), 2.88-0.65 (m, 56H, sp$^3$ H). The chemical structure, with the labeled hydrogen atoms (a-g) and carbon atoms (1-10) used in reference to the identification of NMR peaks, and analysis (above) is presented in FIG. 3, with a proposed homopolymer structure presented in FIG. 4.

It was determined through $^1$H and $^{13}$C NMR as well as computational modelling of the reaction with the hydroxyl radical (FIG. 31, table 2) that polymerization of linalool occurred between $C^7$ and $C^8$, although some of the bonds between $C^1$ and $C^2$ have also participated in polymerization (FIGS. 1-6). The $^{13}$C NMR of linalool shows four carbon peaks in the sp$^2$ region. These signals are present at 145.1 ppm ($C^2$), 132.0 ppm ($C^8$), 124.4 ppm ($C^7$) and 111.8 ppm ($C^1$). The $^{13}$C NMR of the polymer shows two sets of signals in the sp$^2$ region. The series of signals at ~145 ppm correspond to $C^2$ at different positions in the polymer and the series of signals at ~111 ppm correspond to $C^1$ at different positions in the polymer. The loss of $C^7$ and $C^8$ signals in the sp$^2$ region of the $^{13}$C spectra suggest there is no longer an alkene bond between $C^7$ and $C^8$ and that this is therefore the site of polymerization.

Linalool has four alkene hydrogens, $H^A$, $H^{A'}$, $H^B$ and $H^G$. In the $^1$H NMR of the monomer, these signals appear as three doublets of doublets at 5.88 ppm ($H^B$), 5.18 ppm ($H^A$) and 5.03 ppm ($H^{A'}$) and a triplet at 5.09 ppm ($H^G$). The polymer $^1$H NMR shows the presence of signals for $H^A$, $H^{A'}$ and $H^B$ at essentially the same chemical shifts, however the $H^G$ signal is no longer present in the alkene region, further indicating that polymerization has occurred between $C^7$ and $C^8$. The relative integration between the sp$^2$ protons and the sp$^3$ is approximately 3:67, however if polymerization had only occurred between $C^7$ and $C^8$ then it should be 3:15. Therefore, on many of the linalool molecules, both double bonds have participated in polymerization. Because all of the bonds between $C^7$ and $C^8$ have been polymerized, it can be concluded that polymerization occurs more favourably between $C^7$ and $C^8$. We hypothesize that it is because polymerization at this location results in the formation of a more stable tertiary free radical.

The addition of hydroxyl radicals to linalool was also studied computationally to yield further information on the mechanism of polymerization. All reactants and products were optimized at using UB3LYP and a 6-31Gd,p basis set to determine which reaction is the most thermodynamically favorable. It was determined that the addition of a hydroxyl radical to $C^7$ (FIG. 31 reaction a and table 2) is the most energetically favorable addition of the initiator to linalool with a free energy difference of −90.24 kJ/mol. It was also determined that the hydrogen abstraction from linalool's alcohol group is very unlikely as the free energy difference is only −62.41 kJ/mol (FIG. 31 reaction e) and although H atom abstraction via reaction f is the thermodynamic control product, since the addition is observed the polymerization reaction is kinetic controlled via addition to $C^7$. This is due to smaller activation free energy at the temperature in which we performed the polymerization. The computational results correspond with NMR analysis which indicates that polymerization occurs between $C^7$ and $C^8$.

ii. Geraniol Homopolymers

The $^1$H and $^{13}$C NMR of geraniol (FIGS. 9 and 10 respectively), deprotonated geraniol from geraniol with KOH reaction (FIGS. 12 and 13 respectively) and the geraniol polymer by AIBN (FIGS. 15 and 16 respectively) and Geraniol polymerization with $H_2O_2$ (FIGS. 21 and 22 respectively) are presented. FIG. 8 is a structure of the geraniol monomer, with the carbon atoms labelled 1-10 and the hydrogen atoms labelled a-h for the discussion of the nmr spectra. FIG. 14 is a representative structure of the geraniol polymer.

From the NMR's (FIGS. 12 and 13) it is determined that the primary reaction between KOH and geraniol is the deprotonation of the OH group in geraniol. Furthermore comparison of the monomer/deprotonated monomer and the polymer suggest that polymerization occurs at the C2 and C3 carbon atoms based on the absence of the proton peak for their hydrogen atoms. Additionally the loss of peaks in the sp2 range for both the 1H and 13C spectra show the loss of this double bond. We also further observe large peak broadening in the $^1$H NMR of the polymer indicative of a polymer.

iii. Citronellol Homopolymers

The $^1$H and $^{13}$C NMR of citronellol (FIGS. 18 and 19 respectively), and citronellol polymer formed by $H_2O_2$ (FIGS. 25 and 26 respectively) are presented.

From the NMR's (FIGS. 18,19 and 25,26) it is determined that polymerization of the monomer occurred successfully based on the loss of an sp$^2$ proton and carbon signal in the $^1$H and $^{13}$C NMR spectra respectively.

Example 5—Characterization of the Homopolymers by Fourier Transform Infra-Red (FTIR) Spectroscopy The FTIR spectrum was recorded by Thermo Nicolet iS5 FT-Infrared Spectrometer with iD5 ATR Diamond accessory.

i. Linalool Homopolymers

The FTIR spectrum of the linalool polymer is shown in FIG. 7. The key IR absorption frequencies identified for the polymer are (ATR, cm-1): 3416 (br, m, O—H), 2972 (m, C—H), 2942 (m, C—H), 2875 (w, C—H), 2359 (w), 2014 (w), 1715 (m, C=C) 1455 (m), 1374 (m), 1231 (m), 1156 (br, s), 1076 (br, vs), 914 (br, s), 668 (br, m)

The IR spectra of the polymer (FIG. 7) shows significant signal broadening, especially in the fingerprint region. This result is consistent with polymerization and is a result of vibrations in the repeating polymer units occurring at slightly different frequencies as a result of being in slightly different environments.[12] The signal at 1715 results from alkene carbon-carbon stretch and indicates the presence of unsaturation, as was also confirmed by $^1$H and $^{13}$C NMR (example 4). The broad peak at 3416 results from the O—H stretch and confirms the presence of alcohol functional groups in the polymer.

ii. Geraniol Homopolymers

The FTIR spectrum of the geraniol and KOH reaction product is presented in FIG. 11, and shows primarily the deprotonation of the OH functionality. The FTIR of the subsequent polymer, polymerized using AIBN is presented in FIG. 17. The FTIR spectrum of the geraniol polymer, polymerized using $H_2O_2$ is presented in FIG. 23.

iii. Citronellol Homopolymers

The FTIR spectrum of citronellol is presented in FIG. 20, and the polymer, polymerized using $H_2O_2$ is presented in FIG. 24.

Example 6—Characterization of the Homopolymers by Viscosity

Viscosity measurements were performed on a Brookfield Synchro-Lectric LVF Viscometer.

i. Linalool Homopolymers

The viscosities of the homopolymer as well as the linalool monomer were both measured. The viscosity of the polymer in example 1 was determined to be 5760±20 mPa·s while the viscosity of linalool was measured to be only 9.8±0.3 mPa·s, both measured at the 95% confidence level. The more than 500 fold increase in viscosity adds further evidence that polymerization of linalool has been successful, as increasing viscosity of the monomer solution is an indication of polymerization as well as polymer molecular weight.

Furthermore, using the mark-houwink parameters of polyethylene glycol in ethanol as published by Dohmen and coworkers[13], K (0.17) and alfa (0.45) the viscosity average molecular weight of the linalool homopolymer synthesized using hydrogen peroxide was calculated as 1549 g/mol relative to polyethylene glycol. The intrinsic viscosity of the homopolymer in ethanol was determined using the viscosity at polymer concentrations of 2, 1.5, 1.25 and 1 g/ml in ethanol to be 4.6339.

ii. Geraniol Homopolymers

The viscosities of the homopolymer and monomer of geraniol was measured. The viscosity of one of the polymers in example 2 (hydrogen peroxide synthesis) was determined to be 5930±72 mPa·s while the viscosity of geraniol was 14±0.75 mPa·s, both measured at the 95% confidence level. The more than 400 fold increase in viscosity adds further evidence that polymerization of geraniol has been successful, as increasing viscosity of the monomer solution is an indication of polymerization as well as polymer molecular weight.

Furthermore, using the mark-houwink parameters of polyethylene glycol in ethanol as published by Dohmen and coworkers[13], K (0.17) and alfa (0.45) the viscosity average molecular weight of the geraniol homopolymer synthesized using hydrogen peroxide was calculated as 1373 g/mol relative to polyethylene glycol. The intrinsic viscosity of the homopolymer in ethanol was determined using the viscosity at polymer concentrations of 2, 1.5, 1 and 0.5 g/ml in ethanol to be 4.3894.

iii. Citronellol Homopolymers

The viscosities of the homopolymer and monomer of citronellol was measured. The viscosity of the polymer in example 3 was determined to be 3005±11 mPa·s while the viscosity of citronellol was 24.75±0.53 mPa·s, both measured at the 95% confidence level. The more than 100 fold increase in viscosity of pure compounds adds further evidence that polymerization of geraniol has been successful, as increasing viscosity of the monomer solution is an indication of polymerization as well as polymer molecular weight.

Furthermore, using the mark-houwink parameters of polyethylene glycol in ethanol as published by Dohmen and coworkers[13], K (0.17) and alfa (0.45) the viscosity average molecular weight of the citronellol homopolymer synthesized using hydrogen peroxide was calculated as 2005 g/mol relative to polyethylene glycol. The intrinsic viscosity of the homopolymer in ethanol was determined using the viscosity at polymer concentrations of 2, 1.5, 1.25 and 1 g/ml in ethanol to be 5.2044.

Example 7—Characterization of the Homopolymers by Mass Spectrometry

A mass spectrum of the linalool polymer was acquired using ESI, with sodium ions. The spectrum is presented in FIG. 27. From the mass spectrum, the highest identified peak is at 1670 m/z. This corresponds to approximately 10 monomer units, however the mass spectrum is based on a mass/charge ratio and this assumes only one of the OH groups was charged. If multiple charges were present on the polymer then the above number would be the lowest limit for molecular weight. Further molecular weight analysis was done by viscosity measurements as were described above.

Example 8—Characterization of the Homopolymers by Differential Scanning Calorimetry (DSC)

The polymer samples were characterized using differential scanning calorimetry using a TA instruments Q200 DSC instrument. The DSC plots for the citronellol homopolymer, geraniol homopolymer, and linalool homopolymer are presented in FIGS. 28-30 respectively. The glass transition temperatures of these homopolymers are −50.2° C. for the citronellol homopolymer, −40.82° C. for the geraniol homopolymer, and −33.35° C. for the linalool homopolymer Example 9—Characterization of the Anti-Microbial Activity of the Homopolymers Disk inhibition studies were performed for all the synthesized homopolymers to demonstrate their retention of their useful monomeric properties (therapeutic, functionality etc.), and possible impact of polymerization on such properties. The procedure used to conduct the testing is outlined below, with the results of the anti-microbial testing presented in table 1.

In general it is observed that there is an improvement in anti-microbial activity for the linalool homopolymer as compared to the monomer, while the citronellol and geraniol homopolymer show similar to slightly increased activity as compared to their monomers.

Preparation of Bacterial Broth.

Tubes of Tryptic Soy Broth (10 mL/tube,) were prepared according to manufacturer directions (Difco) using aseptic techniques. Bacterial broth of *Escherichia coli, Staphylococcus aureus, Pseudomonas aeruginosa, Proteus hauseri*, and *Bacillus cereus* were prepared in a tissue culture hood by transferring frozen stock culture (−70° C. freezer, prepared from ATCC bacterial quality control strains) of the given bacteria to the broth tube. The *E. coli, S. aureus, P. aeruginosa*, and *P. hauseri* culture tubes were then incubated for 24 hours at 37° C. and the *B. cereus* culture tubes were incubated at 30° C. for 24 hours.

Preparation of Fungal Broth.

Plates of Sabourad Dextrose Agar (Difco) and tubes of Malt Extract Broth (20 mL/tube) were prepared according to manufacturer direction using aseptic techniques. Fungal broths of *Saccharomyces cerevisiae* and *Candida albicans* were prepared in a tissue culture hood by transferring frozen stock culture (−70° C. freezer, prepared from ATCC bought strains) of the given fungi to the broth tube. The *S. cerevisiae* culture tubes were incubated for 48 hours at 30° C. and the *C. albicans* culture tubes were incubated for 48 hours at 37° C.

Fungal broths of *Aspergillus fumigatus* and *Aspergillus niger* were prepared in a tissue culture hood by transferring the frozen stock culture (−70° C. freezer) of the given fungi to a plate of Sabourad Dextrose Agar. The *A. fumigatus* culture plates were incubated for 48 hours at 37° C. and the *A. niger* culture plates were incubated for 72 hours at 25° C. The fungal broth was prepared by using a cork borer to add 2-3 circular pieces of agar containing active fungal growth to distilled water (4.0 mL). A tissue homogenizer was then used to grind the agar and create a suspension of fungal spores.

Preparation of Sample Disks.

Each sample (~15 mg) was dissolved in a solvent (3.000 mL of tetrahydrofuran or 3.000 mL distilled water) depending on the sample's solubility. The sample (20 μL of sample solution or 100 μg of sample was then transferred to a sterile filter paper disk. The disk was then allowed to dry so that all solvent was evaporated and 100 μg of sample remained on the disk.

Preparation of Bacterial Agar Plates.

Plates of Mueller Hinton II Agar (Difco) were prepared according to manufacturer directions using aseptic techniques. The bacterial agar plates were prepared using the bacterial culture broth of *E. coli, S. aureus, P. aeruginosa, P. hauseri*, or *B. cereus* as prepared above after the incubation period. In a tissue culture hood, the given bacterial culture broth solution (300 μL) was transferred to each Mueller Hinton Agar II plate and spread evenly over the agar and allowed to dry for a minimum of 20 minutes. Four sample disks (as prepared above) or control antibiotic disks (pre-made disks) were then places onto each agar plate, one in the center of each quadrant of the plate. The pre-made antimicrobial disks were of Penicillin (10 μg), Tetracycline (30 μg), Chloramphenicol (30 μg) and Ampicillin (10 μg).

The *E. coli, S. aureus, P. aeruginosa*, and *P. hauseri*, plates were incubated for 24 hours at 37° C. and the *B. cereus* plates were incubated for 24 hours at 30° C. The plates were then observed for zones of bacterial growth inhibition. Where a zone of growth inhibition was observed, the diameter of the ring was measured to the closest 0.1 mm using a caliper. An incomplete ring or absence of inhibition zone was ruled a failed test and the compound was ruled inactive against that particular organism. The absence of a uniform bacterial lawn was ruled a failed test and in this case the test would need to be repeated in order to achieve meaningful results.

Preparation of the Fungal Agar Plates.

Plates of Sabourad Dextrose Agar (Difco) were prepared according to manufacture directions using aseptic techniques. The fungal agar plates were prepared using the culture broth of *S. cerevisiae*, *C. albicans*, *A. fumigatus* or *A. niger* as prepared above after the incubation period. In a tissue culture hood, the fungal culture broth solution (200 μL) was transferred to each Sabourad Dextrose Agar plate and spread evenly over the agar and allowed to dry for a minimum of 20 minutes. Four sample disks or control antifungal disks were then places onto each agar plate, one in the center of each quadrant of the plate. The sample disks were prepared as described above and the antifungal disks were pre-made disks of 20 μg of amphotericin B.

The *C. albicans* and *A. fumigfatus* plates were incubated for 24 hours at 37° C., the *A. niger* plates were incubated for 48 hours at 25° C. and the *S. cerevisiae* plates were incubated for 24 hours at 30° C. The plates were then observed for zones of fungal growth inhibition. Where a zone of growth inhibition was observed, the diameter of the ring was measured to the closest 0.1 mm using a caliper. An incomplete ring or absence of inhibition zone was ruled a failed test and the compound was ruled inactive against that particular organism. The absence of a uniform fungal lawn was ruled a failed test and in this case the test would need to be repeated in order to achieve meaningful results.

Example 10—Incorporation of the Homopolymers into Heat Shrink Bandages

Linalool homopolymers were incorporated into bandages, by mixing the homopolymer with cotton bandage squares and vinyl acetate monomer for 24 hrs, after which the monomer was polymerized by free radical polymerization using AIBN.

The resulting composite material (2×2 inch square) was stretched under heat using a heat gun and clamps to an average length of 3.6 inches over 3 samples. The composite was allowed to cool down to room temperature, and the clamps around the material removed. The material was then exposed again to heat from the heat gun, and allowed to shrink towards its original length. When the material stopped visibly shrinking, the heat gun was removed and the material allowed to cool down. Thereafter the final length of the sample was measured to have shrunk to an average length of 2.83 inches, or approx. 21% of its length.

As the cotton and polyvinyl acetate are known to be biocompatible, and the homopolymer antimicrobial, incorporation of antimicrobial terpenoid homopolymer are used to create antimicrobial bandages, and heat shrinkable materials, coatings, and composites for therapeutic, and industrial applications.

TABLES

TABLE 1

Summary of Results of Disk Inhibition Testing of Homopolymers and Monomers of the disclosure.
NI = no inhibition, NR = Experiment repeat (e.g. no lawn etc.) so tests to be repeated.

| Sample | E. Coli | S. Aureus | P. Aeriginosa | P. Hauseri | B. Cereus | A. Niger | S. Cerevisiae | C. Albicans | A. Fumigratus |
|---|---|---|---|---|---|---|---|---|---|
| Linalool | 7.2 | NI | 7.1 | NI | NI | NI | 7.3 | NI | NI |
| Linalool Homopolymer | 8.0 | 10.0 | 8.5 | 14.2 | NI | NI | 7.3 | NR | 8.9 |
| Geraniol | 8.5 | 4.7 | NI | 9.3 | NI | 8.1 | NI | 8.3 | NI |
| Geraniol Polymer (AIBN, KOH) | 8.4 | 5.7 | NI | 8.7 | NI | NI | 7.5 | 6.8 | NI |
| Citronellol | 8.7 | 5.4 | NI | 8.8 | NI | NI | 6.7 | NI | NI |
| Citronellol Polymer ($H_2O_2$) | 7.3 | 5.7 | NI | NI | NI | NI | NI | 8.4 | NI |
| Citronellol Polymer (AIBN, KOH) | 9.0 | 12.0 | NI | 8.1 | NI | 8.0 | NI | 7.3 | NI |
| Amphotericin B (20 μg) | | | | | | 9.7 | 10.2 | 12.9 | 11.4 |
| Ampicillin (10 μg) | 19.7 | 17.9 | 9.1 | 7.2 | NI | | | | |
| Penicillin (10 μg) | 9.4 | 16.9 | NI | 8.1 | NI | | | | |
| Chloramphenicol (30 μg) | 24.4 | 17.8 | 18.7 | 16.7 | 15.7 | | | | |
| Tetracycline (30 μg) | 21.4 | 19.0 | 12.3 | 15.9 | 23.4 | | | | |

TABLE 2

Summary of Results from computational modelling of the reaction between linalool and the hydroxyl radical for the various reaction sites depicted in FIG. 31.

| Reaction | $\Delta G^{o\prime}$ (kJ/mol) |
|---|---|
| Linalool + •OH → A | −90.24 |
| Linalool + •OH → B | −81.91 |
| Linalool + •OH → C | −73.26 |
| Linalool + •OH → D | −80.59 |
| Linalool + •OH → E + $H_2O$ | −62.41 |
| Linalool + •OH → F + $H_2O$ | −147.86 |

REFERENCES (1) Dorman, H. J.; Deans, S. G. Antimicrobial Agents from Plants: Antibacterial Activity of Plant Volatile Oils. *J. Appl. Microbiol.* 2000, 88, 308-316.
(2) Tang, H.; Murphy, C. J.; Zhang, B.; Shen, Y.; Van Kirk, E. a; Murdoch, W. J.; Radosz, M. Curcumin Polymers as Anticancer Conjugates. *Biomaterials* 2010, 31, 7139-7149.
(3) Taylor, P.; Dorman, H. J. D.; Surai, P.; Deans, S. G. Journal of Essential Oil Research In Vitro Antioxidant Activity of a Number of Plant Essential Oils and Phytoconstituents In Vitro Antioxidant Activity of a Number of Plant Essential Oils and Phytoconstituents. *J. Essent. Oil Res.* 2000, 12, 241-248.
(4) Hazan, Z. Therapeutic Uses of Oligomeric and Polymeric Monoterpenes. U.S. Patent 20,120,213,727.
(5) Wilbon, P. A.; Chu, F.; Tang, C. Progress in Renewable Polymers from Natural. *Marcomelecular Rapid Commun.* 2013, 34, 8-37.
(6) Agricultural, F.; Stations, E.; Series, J.; Florida, S. Effect of Pinolene ('8-Pinene Polymer) on Carbaryl Foliar Residues'. *J. Agric. Food Chem.* 1970, 18, 681-684.
(7) Singh, A.; Dwivedi, M. K.; Singh, D. K. Kinetic Study of Copolymerization of Linalool and Methyl Methacrylate Initiated by Selenonium Ylide. *Int. J. Chem. Kinet.* 2011, 43, 43-52.
(8) Shukla, A.; Srivastava, A. K. Synthesis and Characterization of Functional Copolymer of Linalool and Vinyl Acetate: A Kinetic Study. *J. Appl. Polym. Sci.* 2004, 92, 1134-1143.
(9) Shukla, A.; Srivastava, A. K. Determination of Reactivity Ratios and Kinetics of Free Radical Copolymerization of Linalool with Styrene. *Polym. Adv. Technol.* 2004, 15, 445-452.
(10) Shukla, A.; Srivastava, a. K. Kinetics and Mechanism of Copolymerization of Linalool with Acrylonitrile. *J. Macromol. Sci. Part A* 2003, 40, 61-80.
(11) Shukla, A.; Srivastava, A. K. Free Radical Copolymerization of Acrylamide and Linalool with Functional Group as a Pendant. *High Perform. Polym.* 2003, 15, 243-257.
(12) Bower, D. I. *The Vibrational Spectroscopy of Polymers*; Cambridge University Press, 1992; pp. 15-16.
(13) Dohmen, M. P. J.; Pereira, A. M.; Timmer, J. M. K.; Benes, N. E.; Keurentjes, J. T. F. Hydrodynamic Radii of Polyethylene Glycols in Different Solvents Determined from Viscosity Measurements. *J. Chem. Eng. Data* 2008, 53, 63-65.

The invention claimed is:

1. A terpenoid homopolymer selected from the group consisting of polylinalool, polycitronellol, polygerianiol, polynerol, polylasiol, poly-trans-nerolidol and poly-cis-nerolidol having the structures

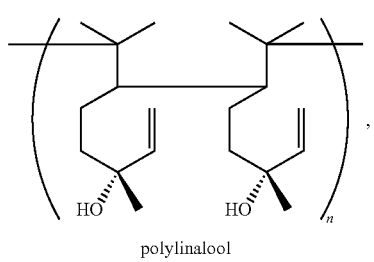
polylinalool

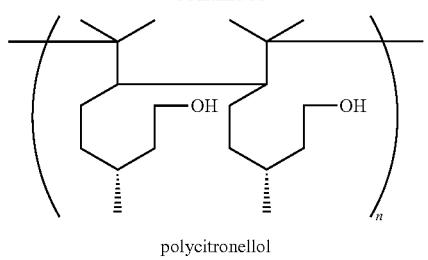
polycitronellol

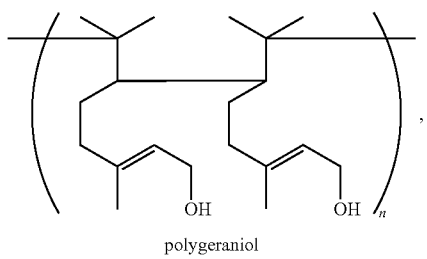
polygeraniol

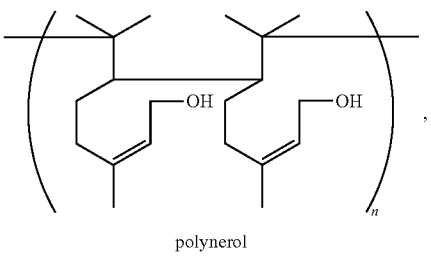
polynerol

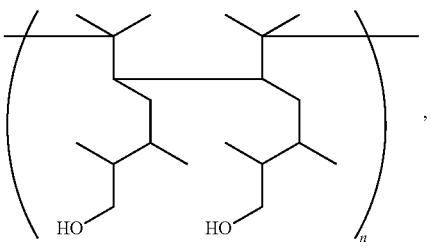
polylasiol

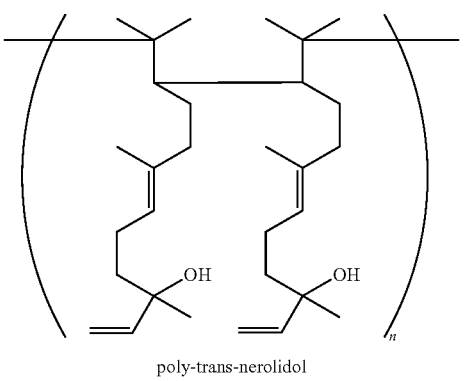
poly-trans-nerolidol

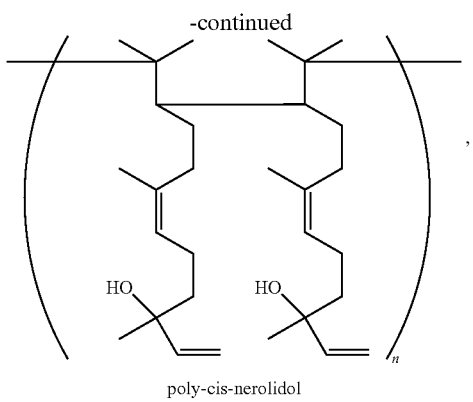

poly-cis-nerolidol wherein n is an integer between 1 and 10,000.

2. The terpenoid homopolymer of claim 1, wherein n is an integer between about 5 and about 1,000.

3. The terpenoid homopolymer of claim 1, wherein n is an integer between about 5 and about 15.

4. The terpenoid homopolymer of claim 1, wherein the terpenoid homopolymer is a functional polyol pre-polymer.

5. The terpenoid homopolymer of claim 1, wherein the terpenoid homopolymer is a functional pre-polymer for urethane chemistry.

6. The terpenoid homopolymer of claim 1, wherein the terpenoid homopolymer has therapeutic, antimicrobial, preservative or insecticidal properties.

7. The terpenoid homopolymer of claim 1, wherein the terpenoid homopolymer is incorporated as an organoleptic agent in a cosmetic formulation.

8. The terpenoid homopolymer of claim 1, wherein the terpenoid homopolymer is incorporated into a finished consumer product or packaging materials to impart antimicrobial or organoleptic properties to the material.

9. The terpenoid homopolymer of claim 1, the terpenoid homopolymer forms a liquid antimicrobial coating by non-covalently bonding to the desired surface or substrate.

10. The terpenoid homopolymer of claim 1, wherein the antimicrobial terpenoid homopolymer is incorporated into bandages, shrink coatings, polymeric and other composite materials for medicinal, protective coatings and packaging applications.

11. The terpenoid homopolymer of claim 1, wherein the terpenoid homopolymer is applied as a film or surface coating by chemical functionalization or reactions of the hydroxyl group with the surface.

12. The terpenoid homopolymer of claim 1, wherein the terpenoid homopolymer is a feedstock for renewable plastic materials.

13. A method of synthesizing a terpenoid homopolymer as defined in claim 1, comprising homopolymerizing a terpenoid monomer selected from the group consisting of linalool, citronellol, geraniol, nerol, lasiol, trans-nerolidol, and cis-nerolidol, the method comprising
  i. Reacting the monomer with a free radical initiator without deprotonation or without protecting groups;
  ii. Optionally deprotonating or protecting the hydroxyl functionality of the monomer prior to polymerization.

14. The method of claim 13, wherein the free radical initiator is selected from the group consisting of hydrogen peroxide, an azo initiator, a halogen initiator, an organic peroxide initiator, an inorganic peroxide initiator, a hydroxyperoxy initiator, a photosensitizer, a photo initiator and a transition metal catalyst capable of generating radicals for polymerization.

15. The method of claim 13, wherein the polymerization is initiated thermally or photoinitiated.

* * * * *